United States Patent
Goerz, Jr.

(10) Patent No.: US 9,493,709 B2
(45) Date of Patent: Nov. 15, 2016

(54) HYBRID FUEL AND METHOD OF MAKING THE SAME

(75) Inventor: David J. Goerz, Jr., Palo Alto, CA (US)

(73) Assignee: Fuelina Technologies, LLC, Menlo Park, CA (US)

( * ) Notice: Subject to any disclaimer, the term of this patent is extended or adjusted under 35 U.S.C. 154(b) by 0 days.

(21) Appl. No.: 13/434,587

(22) Filed: Mar. 29, 2012

(65) Prior Publication Data

US 2012/0297665 A1    Nov. 29, 2012

Related U.S. Application Data

(60) Provisional application No. 61/469,036, filed on Mar. 29, 2011.

(51) Int. Cl.
| | | |
|---|---|---|
| *C10L 1/02* | (2006.01) | |
| *C10L 1/14* | (2006.01) | |
| *B01J 19/08* | (2006.01) | |

(Continued)

(52) U.S. Cl.
CPC ............ *C10G 15/12* (2013.01); *C10G 15/08* (2013.01); *C10L 1/02* (2013.01); *C10L 1/328* (2013.01); *F02D 19/0652* (2013.01); *F02D 19/081* (2013.01); *F02M 27/042* (2013.01); *C10G 2300/1011* (2013.01); *C10G 2300/1025* (2013.01); *C10G 2300/304* (2013.01); *Y02P 30/10* (2015.11); *Y02P 30/20* (2015.11); *Y02T 10/36* (2013.01)

(58) Field of Classification Search
CPC ............. C07C 1/00; C10L 1/02; C10L 1/32; C10L 1/14; C10G 35/00; C10G 1/00; C10B 3/02; B01J 19/08

USPC ........... 44/301, 457, 307; 48/127.5; 585/240, 585/733; 422/186.21, 186.22, 186.28; 208/133

See application file for complete search history.

(56) References Cited

U.S. PATENT DOCUMENTS

| | | |
|---|---|---|
| 2,438,029 A | 3/1948 | Atwell |
| 2,474,845 A | 7/1949 | Jenny et al. |

(Continued)

FOREIGN PATENT DOCUMENTS

| | | |
|---|---|---|
| CA | 1011283 A1 | 5/1977 |
| CA | 1081654 A1 | 7/1980 |

(Continued)

OTHER PUBLICATIONS

Agnew., "Cross-Metathesis of Propane and Methane: A Catalytic Reaction of C_C Bond Cleavage of a Higher Alkane by Methane," Chem. Int. Ed.: 43: 5366-5369 (2004).

(Continued)

*Primary Examiner* — Prem C Singh
*Assistant Examiner* — Chantel Graham
(74) *Attorney, Agent, or Firm* — Wilmer Cutler Pickering Hale and Dorr LLP

(57) ABSTRACT

A hybrid fuel and methods of making the same are disclosed. A process for making a hybrid fuel includes the steps of combining a biofuel emulsion blend and a liquid fuel product to form a hybrid fuel. Optionally, the hybrid fuel can be combined with water in a water-in-oil process and include oxygenate additives and additive packages. A hybrid fuel includes blends of biofuel emulsions and liquid fuel products, including light gas diesel. Optionally, the hybrid fuel can include water, oxygenate additives, and other additive packages.

10 Claims, 13 Drawing Sheets

(51) Int. Cl.

| | | |
|---|---|---|
| C10G 1/00 | (2006.01) | |
| C07C 1/00 | (2006.01) | |
| C10G 35/00 | (2006.01) | |
| C10L 1/32 | (2006.01) | |
| C01B 3/02 | (2006.01) | |
| C10G 15/12 | (2006.01) | |
| C10G 15/08 | (2006.01) | |
| F02D 19/06 | (2006.01) | |
| F02D 19/08 | (2006.01) | |
| F02M 27/04 | (2006.01) | |

(56) References Cited

U.S. PATENT DOCUMENTS

| | | |
|---|---|---|
| 2,667,521 A | 1/1954 | Harney |
| 3,095,286 A | 6/1963 | Andress, Jr. et al. |
| 3,189,531 A | 6/1965 | Hack et al. |
| 3,346,494 A | 10/1967 | Robbins et al. |
| 3,421,870 A | 1/1969 | Sinfelt et al. |
| 3,441,498 A | 4/1969 | Jubin, Jr. et al. |
| 3,639,242 A | 2/1972 | Le Suer |
| 3,755,169 A | 8/1973 | Adams |
| 3,830,301 A | 8/1974 | Holm |
| 3,859,318 A | 1/1975 | Lesuer |
| 3,868,330 A | 2/1975 | Meinhardt et al. |
| 3,876,391 A | 4/1975 | McCoy et al. |
| 3,879,308 A | 4/1975 | Miller |
| 3,948,800 A | 4/1976 | Meinhardt |
| 3,957,854 A | 5/1976 | Miller |
| 3,957,855 A | 5/1976 | Miller |
| 4,031,118 A | 6/1977 | Miller |
| 4,046,519 A | 9/1977 | Piotrowski |
| 4,158,594 A | 6/1979 | Becker et al. |
| 4,185,594 A | 1/1980 | Perilstein |
| 4,193,864 A | 3/1980 | Chang |
| 4,225,456 A | 9/1980 | Schmidt et al. |
| 4,248,720 A | 2/1981 | Coupland et al. |
| 4,329,249 A | 5/1982 | Forsberg |
| 4,368,133 A | 1/1983 | Forsberg |
| 4,389,303 A | 6/1983 | Simo et al. |
| 4,419,466 A | 12/1983 | Hopkins |
| 4,447,348 A | 5/1984 | Forsberg |
| 4,448,703 A | 5/1984 | Forsberg |
| 4,465,889 A | 8/1984 | Anthony et al. |
| 4,471,091 A | 9/1984 | Hayashi |
| 4,486,573 A | 12/1984 | Hayashi |
| 4,489,194 A | 12/1984 | Hayashi |
| 4,493,761 A | 1/1985 | Hensley, Jr. et al. |
| 4,509,955 A | 4/1985 | Hayashi |
| 4,526,586 A | 7/1985 | Schwab et al. |
| 4,559,155 A | 12/1985 | Dorer, Jr. et al. |
| 4,564,460 A | 1/1986 | Dorer, Jr. et al. |
| 4,566,961 A | 1/1986 | Diaz et al. |
| 4,566,983 A | 1/1986 | Hayashi |
| 4,575,526 A | 3/1986 | Dorer, Jr. et al. |
| 4,596,663 A | 6/1986 | Hayashi |
| 4,613,342 A | 9/1986 | Dorer, Jr. et al. |
| 4,618,450 A | 10/1986 | Higgins |
| 4,619,967 A | 10/1986 | Emerson et al. |
| 4,623,684 A | 11/1986 | Dorer, Jr. et al. |
| 4,666,620 A | 5/1987 | Forsberg |
| 4,687,570 A | 8/1987 | Sundaram et al. |
| 4,687,590 A | 8/1987 | Haack |
| 4,706,751 A | 11/1987 | Gondouin |
| 4,708,753 A | 11/1987 | Forsberg |
| 4,710,248 A | 12/1987 | Yates et al. |
| 4,744,796 A | 5/1988 | Hazbun et al. |
| 4,752,383 A | 6/1988 | McKay et al. |
| 4,767,449 A | 8/1988 | Rosen et al. |
| 4,770,670 A | 9/1988 | Hazbun et al. |
| 4,818,309 A | 4/1989 | Yabsley et al. |
| 4,828,633 A | 5/1989 | Forsberg |
| 4,832,868 A | 5/1989 | Schmid et al. |
| 4,840,687 A | 6/1989 | Forsberg et al. |
| 4,844,756 A | 7/1989 | Forsberg |
| 4,846,985 A | 7/1989 | Rizvi et al. |
| 4,863,534 A | 9/1989 | Forsberg |
| 4,919,178 A | 4/1990 | Riga et al. |
| 4,936,933 A | 6/1990 | Yabsley et al. |
| 4,950,831 A | 8/1990 | Staton et al. |
| 4,957,651 A | 9/1990 | Schwind |
| 5,007,973 A | 4/1991 | Trapp et al. |
| 5,015,349 A | 5/1991 | Suib et al. |
| 5,019,355 A | 5/1991 | Sackinger |
| 5,041,622 A | 8/1991 | LeSuer |
| 5,047,175 A | 9/1991 | Forsberg |
| 5,069,775 A | 12/1991 | Grosboll |
| 5,110,452 A | 5/1992 | Meyer et al. |
| 5,120,430 A | 6/1992 | Morgan |
| 5,129,972 A | 7/1992 | Riga et al. |
| 5,131,993 A | 7/1992 | Suib et al. |
| 5,177,045 A | 1/1993 | Anthony et al. |
| 5,181,998 A | 1/1993 | Murphy et al. |
| 5,213,697 A | 5/1993 | Vinci et al. |
| 5,233,113 A | 8/1993 | Periana et al. |
| 5,259,851 A | 11/1993 | Genova et al. |
| 5,269,909 A | 12/1993 | Ovalles et al. |
| 5,283,235 A | 2/1994 | Bush et al. |
| 5,330,662 A | 7/1994 | Jahnke et al. |
| 5,336,439 A | 8/1994 | Forsberg et al. |
| 5,344,306 A | 9/1994 | Brown et al. |
| 5,345,011 A | 9/1994 | Durante et al. |
| 5,360,458 A | 11/1994 | Forsberg et al. |
| 5,397,399 A | 3/1995 | Lownds |
| 5,401,341 A | 3/1995 | Forsberg et al. |
| 5,407,500 A | 4/1995 | Forsberg et al. |
| 5,422,024 A | 6/1995 | Vickerman et al. |
| 5,427,747 A | 6/1995 | Kong et al. |
| 5,484,542 A | 1/1996 | Cahoon et al. |
| 5,501,714 A | 3/1996 | Valentine et al. |
| 5,527,491 A | 6/1996 | Riga et al. |
| 5,584,222 A | 12/1996 | Engsbr.ang.ten et al. |
| 5,593,953 A | 1/1997 | Malchow, Jr. |
| 5,620,946 A | 4/1997 | Jahnke et al. |
| 5,633,220 A | 5/1997 | Cawiezel et al. |
| 5,637,557 A | 6/1997 | Jahnke et al. |
| 5,693,106 A | 12/1997 | Peter-Hoblyn et al. |
| 5,809,774 A | 9/1998 | Peter-Hoblyn et al. |
| 5,851,429 A | 12/1998 | Magyar |
| 5,856,279 A | 1/1999 | Baker |
| 5,891,829 A | 4/1999 | Vallejos et al. |
| 5,906,664 A | 5/1999 | Basu et al. |
| 5,920,031 A | 7/1999 | Jahnke |
| 5,936,194 A | 8/1999 | Marlow et al. |
| 6,054,493 A | 4/2000 | Bush |
| 6,110,378 A | 8/2000 | Anthony et al. |
| 6,130,260 A | 10/2000 | Hall et al. |
| 6,147,036 A | 11/2000 | Baker |
| 6,159,432 A | 12/2000 | Mallinson et al. |
| 6,176,893 B1 | 1/2001 | Bush |
| 6,190,427 B1 | 2/2001 | Ahmed |
| 6,200,398 B1 | 3/2001 | Bush |
| 6,207,839 B1 | 3/2001 | Baker |
| 6,229,060 B1 | 5/2001 | Vidal et al. |
| 6,280,485 B1 | 8/2001 | Daly et al. |
| 6,323,247 B1 | 11/2001 | Hall et al. |
| 6,326,407 B1 | 12/2001 | Eliasson et al. |
| 6,368,366 B1 | 4/2002 | Langer et al. |
| 6,368,367 B1 | 4/2002 | Langer et al. |
| 6,375,832 B1 | 4/2002 | Eliasson et al. |
| 6,383,237 B1 | 5/2002 | Langer et al. |
| 6,386,149 B1 | 5/2002 | Coleman et al. |
| 6,419,714 B2 | 7/2002 | Thompson et al. |
| 6,479,427 B1 | 11/2002 | Anthony et al. |
| 6,530,964 B2 | 3/2003 | Langer et al. |
| 6,538,162 B2 | 3/2003 | Chang et al. |
| 6,593,377 B1 | 7/2003 | Harford et al. |
| 6,602,920 B2 | 8/2003 | Hall et al. |
| 6,606,856 B1 | 8/2003 | Brown et al. |
| 6,630,596 B2 | 10/2003 | Boer |
| 6,648,929 B1 | 11/2003 | Daly et al. |
| 6,652,607 B2 | 11/2003 | Langer et al. |
| 6,716,801 B2 | 4/2004 | Martin |
| 6,725,653 B2 | 4/2004 | Brown et al. |

(56) References Cited

U.S. PATENT DOCUMENTS

| | | |
|---|---|---|
| 6,727,397 B2 | 4/2004 | Basset et al. |
| 6,748,905 B2 | 6/2004 | Duncan et al. |
| 6,780,209 B1 | 8/2004 | Filippini et al. |
| 6,800,154 B1 | 10/2004 | Carey et al. |
| 6,823,822 B2 | 11/2004 | Duncan et al. |
| 6,827,749 B2 | 12/2004 | Westfall et al. |
| 6,858,046 B2 | 2/2005 | Daly et al. |
| 6,913,630 B2 | 7/2005 | Filippini et al. |
| 6,923,890 B2 | 8/2005 | Ricatto et al. |
| 6,929,707 B2 | 8/2005 | Mullay et al. |
| 6,933,263 B2 | 8/2005 | Manka et al. |
| 6,939,420 B2 | 9/2005 | Pollack |
| 6,949,235 B2 | 9/2005 | Brown et al. |
| 6,951,589 B2 | 10/2005 | Pollack et al. |
| 7,028,468 B2 | 4/2006 | Brown et al. |
| 7,029,636 B2 | 4/2006 | Ricatto et al. |
| 7,044,988 B2 | 5/2006 | Filippini et al. |
| 7,119,240 B2 | 10/2006 | Hall et al. |
| 7,176,174 B2 | 2/2007 | Filippini et al. |
| 7,229,481 B2 | 6/2007 | Clark et al. |
| 7,270,743 B2 | 9/2007 | Freel et al. |
| 7,307,104 B2 | 12/2007 | Qiu et al. |
| 7,309,684 B2 | 12/2007 | Filippini et al. |
| 7,329,719 B2 | 2/2008 | Pavlin |
| 7,378,564 B2 | 5/2008 | Basset et al. |
| 7,413,583 B2 | 8/2008 | Langer et al. |
| 7,427,303 B2 | 9/2008 | Sarin et al. |
| 7,435,707 B2 | 10/2008 | Langer et al. |
| 7,451,618 B2 | 11/2008 | Ansorge et al. |
| 7,473,814 B2 | 1/2009 | Basset et al. |
| 7,479,576 B1 | 1/2009 | Hassan et al. |
| 7,482,496 B2 | 1/2009 | Hassan et al. |
| 7,482,497 B2 | 1/2009 | Hassan et al. |
| 7,484,358 B2 | 2/2009 | Cho et al. |
| 7,491,247 B1 | 2/2009 | Jakush et al. |
| 7,491,279 B1 | 2/2009 | Baker |
| 7,491,856 B2 | 2/2009 | Hassan et al. |
| 7,494,574 B2 | 2/2009 | Kong et al. |
| 7,501,054 B2 | 3/2009 | Galiasso |
| 7,501,374 B2 | 3/2009 | Galiasso |
| 7,592,493 B2 | 9/2009 | Hassan et al. |
| 7,642,292 B2 | 1/2010 | Severinsky |
| 7,645,305 B1 | 1/2010 | Coleman et al. |
| 7,651,984 B2 | 1/2010 | Cook et al. |
| 7,652,174 B2 | 1/2010 | Hassan et al. |
| 7,652,175 B2 | 1/2010 | Hassan et al. |
| 7,659,431 B2 | 2/2010 | Hassan et al. |
| 7,691,953 B2 | 4/2010 | Hassan et al. |
| 7,696,391 B2 | 4/2010 | Hassan et al. |
| 7,704,288 B2 | 4/2010 | Rivas et al. |
| 7,721,719 B2 | 5/2010 | Okajima et al. |
| 7,722,688 B2 | 5/2010 | Filippini et al. |
| 7,736,400 B2 | 6/2010 | Rabovitser et al. |
| 7,749,481 B2 | 7/2010 | Hassan et al. |
| 7,750,188 B2 | 7/2010 | Hassan et al. |
| 7,759,535 B2 | 7/2010 | Iaccino et al. |
| 7,762,715 B2 | 7/2010 | Gordon et al. |
| 7,772,447 B2 | 8/2010 | Iaccino et al. |
| 7,790,018 B2 | 9/2010 | Khan |
| 7,806,947 B2 | 10/2010 | Gunnerman et al. |
| 7,842,184 B2 | 11/2010 | Hassan et al. |
| 7,884,250 B2 | 2/2011 | Hassan et al. |
| 7,897,124 B2 | 3/2011 | Gunnerman et al. |
| 7,949,574 B2 | 5/2011 | Patel et al. |
| 8,052,946 B2 | 11/2011 | Dighe et al. |
| 8,097,166 B2 | 1/2012 | Nakashima |
| 8,728,182 B2 | 5/2014 | Sirdeshpande et al. |
| 2002/0000085 A1 | 1/2002 | Hall et al. |
| 2002/0088167 A1 | 7/2002 | Filippini et al. |
| 2002/0116868 A1 | 8/2002 | Westfall et al. |
| 2002/0129541 A1 | 9/2002 | Daly et al. |
| 2003/0019552 A1 | 1/2003 | Pollack et al. |
| 2003/0065058 A1 | 4/2003 | Piedrahita et al. |
| 2003/0138373 A1 | 7/2003 | Graham et al. |
| 2003/0164147 A1 | 9/2003 | Duncan et al. |
| 2003/0221360 A1 | 12/2003 | Brown et al. |
| 2004/0002553 A1 | 1/2004 | Hall et al. |
| 2004/0016479 A1 | 1/2004 | Mullay et al. |
| 2004/0020574 A1 | 2/2004 | Pollack |
| 2004/0053791 A1 | 3/2004 | Langer et al. |
| 2004/0093789 A1 | 5/2004 | Hart et al. |
| 2004/0093790 A1 | 5/2004 | Baker et al. |
| 2004/0111955 A1 | 6/2004 | Mullay et al. |
| 2004/0111956 A1 | 6/2004 | Westfall et al. |
| 2004/0111957 A1 | 6/2004 | Filippini et al. |
| 2004/0139931 A1 | 7/2004 | Duncan et al. |
| 2004/0176263 A1 | 9/2004 | Filippini et al. |
| 2004/0194367 A1 | 10/2004 | Clark et al. |
| 2004/0235678 A1 | 11/2004 | Di Biase et al. |
| 2004/0235684 A1 | 11/2004 | Cook et al. |
| 2004/0244277 A1 | 12/2004 | Baker et al. |
| 2004/0248747 A1 | 12/2004 | Mayhew et al. |
| 2005/0000149 A1 | 1/2005 | Moncrieff et al. |
| 2005/0008906 A1 | 1/2005 | Varadaraj et al. |
| 2005/0019624 A1 | 1/2005 | Varadaraj et al. |
| 2005/0019625 A1 | 1/2005 | Varadaraj et al. |
| 2005/0022445 A1 | 2/2005 | Sarin et al. |
| 2005/0027020 A1 | 2/2005 | Steynberg |
| 2005/0039381 A1 | 2/2005 | Langer et al. |
| 2005/0049316 A1 | 3/2005 | Burrington et al. |
| 2005/0060928 A1 | 3/2005 | Oldfield et al. |
| 2005/0097812 A1 | 5/2005 | Guffogg et al. |
| 2005/0115146 A1 | 6/2005 | Jackson et al. |
| 2005/0120619 A1 | 6/2005 | Koch et al. |
| 2005/0132640 A1 | 6/2005 | Kelly et al. |
| 2005/0150155 A1 | 7/2005 | Waldron et al. |
| 2005/0183324 A1 | 8/2005 | Marelli |
| 2005/0215441 A1 | 9/2005 | Mackney et al. |
| 2005/0250863 A1 | 11/2005 | Green et al. |
| 2005/0262759 A1 | 12/2005 | Tort et al. |
| 2005/0288541 A1 | 12/2005 | Sherwood |
| 2006/0005463 A1 | 1/2006 | Gernon et al. |
| 2006/0005464 A1 | 1/2006 | Gernon et al. |
| 2006/0048443 A1 | 3/2006 | Filippini et al. |
| 2006/0054865 A1 | 3/2006 | Smith et al. |
| 2006/0075680 A1 | 4/2006 | Tort et al. |
| 2006/0117647 A1 | 6/2006 | Rivolta et al. |
| 2006/0123695 A1 | 6/2006 | D'Elia et al. |
| 2006/0135838 A1 | 6/2006 | Bagherzadeh et al. |
| 2006/0162237 A1 | 7/2006 | Mullay et al. |
| 2006/0162240 A1 | 7/2006 | Filippini et al. |
| 2006/0204461 A1 | 9/2006 | Pavlin |
| 2006/0236596 A1 | 10/2006 | Baxter |
| 2006/0287560 A1 | 12/2006 | Xie |
| 2007/0027046 A1 | 2/2007 | Friend et al. |
| 2007/0028507 A1 | 2/2007 | Strey et al. |
| 2007/0033861 A1 | 2/2007 | Varadaraj et al. |
| 2007/0044373 A1 | 3/2007 | Yao et al. |
| 2007/0056534 A1 | 3/2007 | Verstallen |
| 2007/0059567 A9 | 3/2007 | Varadaraj et al. |
| 2007/0060781 A1 | 3/2007 | Goldman et al. |
| 2007/0083073 A1 | 4/2007 | Bagherzadeh et al. |
| 2007/0119529 A1 | 5/2007 | Hobson et al. |
| 2007/0124989 A1 | 6/2007 | Eickhoff et al. |
| 2007/0124991 A1 | 6/2007 | Reaney et al. |
| 2007/0142481 A1 | 6/2007 | Steynberg et al. |
| 2007/0175088 A1 | 8/2007 | Selkirk |
| 2007/0199238 A1 | 8/2007 | Hooker |
| 2007/0238905 A1 | 10/2007 | Arredondo et al. |
| 2007/0254969 A1 | 11/2007 | Olah et al. |
| 2007/0261293 A1 | 11/2007 | Tajima et al. |
| 2007/0294935 A1 | 12/2007 | Waldron et al. |
| 2008/0028674 A1 | 2/2008 | Jackson et al. |
| 2008/0060258 A1 | 3/2008 | Rivas et al. |
| 2008/0120898 A1 | 5/2008 | Song et al. |
| 2008/0161588 A1 | 7/2008 | Hassan et al. |
| 2008/0172928 A1 | 7/2008 | Loggers et al. |
| 2008/0178520 A1 | 7/2008 | Church |
| 2008/0207473 A1 | 8/2008 | Startin et al. |
| 2008/0229655 A1 | 9/2008 | Hobson et al. |
| 2008/0233045 A1 | 9/2008 | Ozkan et al. |
| 2008/0250701 A1 | 10/2008 | Van De Berg et al. |
| 2008/0281136 A1 | 11/2008 | Bagherzadeh et al. |
| 2008/0282604 A1 | 11/2008 | Awang et al. |

(56) References Cited

U.S. PATENT DOCUMENTS

| | | |
|---|---|---|
| 2008/0295389 A1 | 12/2008 | Moncrieff et al. |
| 2008/0305539 A1 | 12/2008 | Hickey et al. |
| 2009/0000131 A1 | 1/2009 | Shafer |
| 2009/0000941 A1* | 1/2009 | Kropf .................... 204/157.62 |
| 2009/0000986 A1 | 1/2009 | Hassan et al. |
| 2009/0000989 A1 | 1/2009 | Hassan et al. |
| 2009/0001017 A1 | 1/2009 | Hassan et al. |
| 2009/0001188 A1 | 1/2009 | Hassan et al. |
| 2009/0001316 A1 | 1/2009 | Hassan et al. |
| 2009/0001320 A1 | 1/2009 | Hassan et al. |
| 2009/0003126 A1 | 1/2009 | Hassan et al. |
| 2009/0005521 A1 | 1/2009 | Hassan et al. |
| 2009/0005552 A1 | 1/2009 | Hassan et al. |
| 2009/0005553 A1 | 1/2009 | Hassan et al. |
| 2009/0005578 A1 | 1/2009 | Hassan et al. |
| 2009/0005585 A1 | 1/2009 | Hassan et al. |
| 2009/0005587 A1 | 1/2009 | Hassan et al. |
| 2009/0005588 A1 | 1/2009 | Hassan et al. |
| 2009/0005589 A1 | 1/2009 | Hassan et al. |
| 2009/0005591 A1 | 1/2009 | Hassan et al. |
| 2009/0005592 A1 | 1/2009 | Hassan et al. |
| 2009/0005598 A1 | 1/2009 | Hassan et al. |
| 2009/0005602 A1 | 1/2009 | Hassan et al. |
| 2009/0005604 A1 | 1/2009 | Hassan et al. |
| 2009/0005605 A1 | 1/2009 | Hassan et al. |
| 2009/0005606 A1 | 1/2009 | Hassan et al. |
| 2009/0005608 A1 | 1/2009 | Hassan et al. |
| 2009/0005609 A1 | 1/2009 | Hassan et al. |
| 2009/0005610 A1 | 1/2009 | Hassan et al. |
| 2009/0005611 A1 | 1/2009 | Hassan et al. |
| 2009/0005612 A1 | 1/2009 | Hassan et al. |
| 2009/0005613 A1 | 1/2009 | Hassan et al. |
| 2009/0005615 A1 | 1/2009 | Hassan et al. |
| 2009/0005619 A1 | 1/2009 | Hassan et al. |
| 2009/0005621 A1 | 1/2009 | Hassan et al. |
| 2009/0005622 A1 | 1/2009 | Hassan et al. |
| 2009/0005625 A1 | 1/2009 | Hassan et al. |
| 2009/0009108 A1 | 1/2009 | Hongo |
| 2009/0018286 A1 | 1/2009 | Hassan et al. |
| 2009/0018596 A1 | 1/2009 | Kieval |
| 2009/0024968 A1 | 1/2009 | Yamada |
| 2009/0036694 A1 | 2/2009 | Hassan et al. |
| 2009/0048476 A1 | 2/2009 | Rappas et al. |
| 2009/0049736 A1 | 2/2009 | Suraci et al. |
| 2009/0049737 A1 | 2/2009 | Suraci et al. |
| 2009/0049740 A1 | 2/2009 | Hurst |
| 2009/0084707 A1 | 4/2009 | Gil |
| 2009/0090055 A1 | 4/2009 | Ohtsuka |
| 2009/0090056 A1 | 4/2009 | Ohtsuka |
| 2009/0118380 A1 | 5/2009 | Del Gaudio et al. |
| 2009/0120416 A1 | 5/2009 | Wey |
| 2009/0136392 A1 | 5/2009 | Hassan et al. |
| 2009/0136393 A1 | 5/2009 | Hassan et al. |
| 2009/0136395 A1 | 5/2009 | Hassan et al. |
| 2009/0136396 A1 | 5/2009 | Hassan et al. |
| 2009/0145392 A1 | 6/2009 | Clark et al. |
| 2009/0151231 A1 | 6/2009 | Lee et al. |
| 2009/0152168 A1 | 6/2009 | Siskin et al. |
| 2009/0165361 A1 | 7/2009 | Rappas et al. |
| 2009/0165376 A1 | 7/2009 | Lau et al. |
| 2009/0165379 A1 | 7/2009 | Rappas |
| 2009/0165380 A1 | 7/2009 | Lau et al. |
| 2009/0165381 A1 | 7/2009 | Robinson |
| 2009/0165382 A1 | 7/2009 | Rappas et al. |
| 2009/0165383 A1 | 7/2009 | Rappas et al. |
| 2009/0165384 A1 | 7/2009 | Lau et al. |
| 2009/0166588 A1 | 7/2009 | Spitz et al. |
| 2009/0169448 A1 | 7/2009 | Rappas et al. |
| 2009/0169449 A1 | 7/2009 | Rappas et al. |
| 2009/0170968 A1 | 7/2009 | Nahas et al. |
| 2009/0180940 A1 | 7/2009 | Hassan et al. |
| 2009/0185963 A1 | 7/2009 | Hanson |
| 2009/0188157 A1 | 7/2009 | Holloway, Jr. et al. |
| 2009/0193708 A1 | 8/2009 | Wang |
| 2009/0205254 A1 | 8/2009 | Zhu et al. |
| 2009/0208382 A1 | 8/2009 | Hassan et al. |
| 2009/0217575 A1 | 9/2009 | Raman et al. |
| 2009/0217582 A1 | 9/2009 | May et al. |
| 2009/0217584 A1 | 9/2009 | Raman et al. |
| 2009/0217585 A1 | 9/2009 | Raman et al. |
| 2009/0217586 A1 | 9/2009 | Rappas et al. |
| 2009/0217587 A1 | 9/2009 | Raman et al. |
| 2009/0217588 A1 | 9/2009 | Hippo et al. |
| 2009/0217589 A1 | 9/2009 | Robinson |
| 2009/0217590 A1 | 9/2009 | Rappas et al. |
| 2009/0218424 A1 | 9/2009 | Hauserman |
| 2009/0220406 A1 | 9/2009 | Rahman |
| 2009/0229182 A1 | 9/2009 | Raman et al. |
| 2009/0234168 A1 | 9/2009 | Butler et al. |
| 2009/0238750 A1* | 9/2009 | Bosetti et al. ............. 423/573.1 |
| 2009/0246120 A1 | 10/2009 | Raman et al. |
| 2009/0247804 A1 | 10/2009 | Sauer et al. |
| 2009/0249682 A1 | 10/2009 | Gunnerman et al. |
| 2009/0250330 A1 | 10/2009 | Gunnerman et al. |
| 2009/0259080 A1 | 10/2009 | Raman et al. |
| 2009/0260278 A1 | 10/2009 | Klausmeier |
| 2009/0260280 A1 | 10/2009 | Klausmeier et al. |
| 2009/0260287 A1 | 10/2009 | Lau |
| 2009/0282729 A1 | 11/2009 | Guzmann et al. |
| 2009/0300969 A1 | 12/2009 | Martin |
| 2009/0313885 A1 | 12/2009 | Wang |
| 2009/0321331 A1 | 12/2009 | Hassan et al. |
| 2009/0324458 A1 | 12/2009 | Robinson et al. |
| 2009/0324459 A1 | 12/2009 | Robinson et al. |
| 2009/0324460 A1 | 12/2009 | Robinson et al. |
| 2009/0324461 A1 | 12/2009 | Robinson et al. |
| 2009/0324462 A1 | 12/2009 | Robinson et al. |
| 2010/0000502 A1 | 1/2010 | Hassan et al. |
| 2010/0004419 A1 | 1/2010 | Hassan et al. |
| 2010/0004493 A1 | 1/2010 | Porter et al. |
| 2010/0015015 A1 | 1/2010 | Hassan et al. |
| 2010/0015019 A1 | 1/2010 | Hassan et al. |
| 2010/0018118 A1 | 1/2010 | Hassan et al. |
| 2010/0028735 A1 | 2/2010 | Basset et al. |
| 2010/0037513 A1 | 2/2010 | Petrucci et al. |
| 2010/0064577 A1 | 3/2010 | Gunnerman et al. |
| 2010/0071262 A1 | 3/2010 | Robinson et al. |
| 2010/0076235 A1 | 3/2010 | Reiling et al. |
| 2010/0080736 A1 | 4/2010 | Hassan et al. |
| 2010/0087688 A1 | 4/2010 | Miller et al. |
| 2010/0088949 A1 | 4/2010 | Reed |
| 2010/0092347 A1 | 4/2010 | Hassan et al. |
| 2010/0092354 A1 | 4/2010 | Hassan et al. |
| 2010/0095580 A1 | 4/2010 | Suzuki |
| 2010/0101978 A1 | 4/2010 | Gordon et al. |
| 2010/0108492 A1 | 5/2010 | Ishmukhametov et al. |
| 2010/0111786 A1 | 5/2010 | Hassan et al. |
| 2010/0114061 A1 | 5/2010 | Hassan et al. |
| 2010/0115828 A1 | 5/2010 | Rehavi et al. |
| 2010/0120926 A1 | 5/2010 | Robinson et al. |
| 2010/0121125 A1 | 5/2010 | Hippo et al. |
| 2010/0122488 A1 | 5/2010 | Fukai |
| 2010/0126059 A1 | 5/2010 | Shiode et al. |
| 2010/0140135 A1 | 6/2010 | Gunnerman et al. |
| 2010/0147764 A1 | 6/2010 | Hassan et al. |
| 2010/0161029 A1 | 6/2010 | Filippini et al. |
| 2010/0168477 A1 | 7/2010 | Hassan et al. |
| 2010/0168494 A1 | 7/2010 | Rappas et al. |
| 2010/0168495 A1 | 7/2010 | Rappas et al. |
| 2010/0170142 A1 | 7/2010 | Posselt et al. |
| 2010/0172939 A1 | 7/2010 | Shaari |
| 2010/0179232 A1 | 7/2010 | Robinson et al. |
| 2010/0183486 A1 | 7/2010 | Hassan et al. |
| 2010/0186288 A1 | 7/2010 | Ishiguro et al. |
| 2010/0199545 A1 | 8/2010 | Hassan et al. |
| 2010/0199547 A1 | 8/2010 | Reed |
| 2010/0200487 A1 | 8/2010 | Hassan et al. |
| 2010/0212893 A1 | 8/2010 | Moini Araghi et al. |
| 2010/0217039 A1 | 8/2010 | Hassan et al. |
| 2010/0222615 A1 | 9/2010 | Hassan et al. |
| 2010/0236984 A1 | 9/2010 | Brookhart et al. |
| 2010/0256245 A1 | 10/2010 | Iaccino et al. |
| 2010/0260649 A1 | 10/2010 | Jorgensen |
| 2010/0266465 A1 | 10/2010 | Hassan et al. |

(56) References Cited

U.S. PATENT DOCUMENTS

| | | | |
|---|---|---|---|
| 2010/0276165 A1 | 11/2010 | Hobson et al. | |
| 2010/0287835 A1 | 11/2010 | Reiling et al. | |
| 2010/0287836 A1 | 11/2010 | Robinson et al. | |
| 2010/0292350 A1 | 11/2010 | Robinson et al. | |
| 2010/0294699 A1 | 11/2010 | Hassan et al. | |
| 2010/0313751 A1 | 12/2010 | Hassan et al. | |
| 2010/0314583 A1 | 12/2010 | Banerjee | |
| 2010/0317748 A1 | 12/2010 | Hassan et al. | |
| 2010/0324308 A1 | 12/2010 | Hassan et al. | |
| 2010/0324349 A1 | 12/2010 | Gunnerman et al. | |
| 2010/0329944 A1 | 12/2010 | Hassan et al. | |
| 2011/0048251 A1* | 3/2011 | Bardenshtein et al. | 99/451 |
| 2011/0049014 A1 | 3/2011 | Gunnerman et al. | |
| 2011/0056120 A1 | 3/2011 | Teo | |
| 2011/0190565 A1* | 8/2011 | Novoselov | B01J 19/088 585/700 |
| 2012/0088945 A1* | 4/2012 | Yao et al. | 585/357 |
| 2012/0199795 A1 | 8/2012 | Gorodetsky et al. | |
| 2012/0261391 A1 | 10/2012 | Ihde et al. | |

FOREIGN PATENT DOCUMENTS

| | | | |
|---|---|---|---|
| CA | 2385107 A1 | 4/2001 | |
| CA | 2400188 A1 | 8/2001 | |
| CA | 2700126 A1 | 4/2009 | |
| CN | 1590297 A | 3/2005 | |
| CN | 101506480 A | 8/2009 | |
| EP | 101815 A1 | 3/1984 | |
| EP | 984827 A1 | 3/2000 | |
| EP | 1163315 A1 | 12/2001 | |
| EP | 1563041 A1 | 8/2005 | |
| EP | 1754532 A2 | 2/2007 | |
| EP | 2022772 A1 | 2/2009 | |
| FR | 2373328 A1 | 7/1978 | |
| GB | 925089 A | 5/1963 | |
| GB | 2434372 A | 7/2007 | |
| PL | 209944 B1 | 11/2011 | |
| WO | WO-9503374 A1 | 2/1995 | |
| WO | WO-9818884 A2 | 5/1998 | |
| WO | WO-9850139 A1 | 11/1998 | |
| WO | WO-0053699 A1 | 9/2000 | |
| WO | WO-03104173 A1 | 12/2003 | |
| WO | WO-2004010454 A2 | 1/2004 | |
| WO | WO-2007083106 A2 | 7/2007 | |
| WO | WO-2008010253 | 1/2008 | |
| WO | WO-2008010253 A2 | 1/2008 | |
| WO | WO-2010069582 A1 | 6/2010 | |
| WO | WO-2010093553 A2 | 8/2010 | |
| WO | WO-2011093736 A1 | 8/2011 | |
| WO | WO-2011119274 A1 | 9/2011 | |

OTHER PUBLICATIONS

Ahmed, W.H. and Basel, I.I., "Innovative Techniques for Two-Phase Flow Measurements," Recent Patents on Electrical Engineering, vol. 1: 1-13 (2008).
Alcock, W.G. et al., "Chemical Reactions of Methane in a Triboelectric Discharge," Can. J. Chem., vol. 50: 3813-3820 (1972).
Anderson, A.B. and Maloney, J.J. "Activation of Methane on Iron, Nickel, Platinum Surfaces. A Molecular Orbital Study," Case Western Reserve University. pp. 291-298. Date is unavailable.
Anunziata, O.A. and Cussa, J. "Methane Activation Process: Simultaneous Optimization of Methan Conversion and Aromatic Yeilds using Zn-XSM-11 Zeolite," The Open Process Chemistry Journal, vol. 3: 7-16 (2010).
Basset, J-M, "From Material Science to Single Site Catalysis," University of Lyon, France KFUPM-KAUST Workshop May 5-6, 2009; KFUPM Dhahran, Saudi Arabia. Abstract only. 1 page.
Basset, J.M., "Direct Conversion of Ethylene to Propylene," www.kufpm.edu.sa/catsymp/symp%2019th/PAPERS/19Basset.doc; King Abdullah University of Science and Technology; Thuwal, Saudi Arabia and Universty of Lyon (1918). 1 page.
Bassett, "Modern Surface Organmetallic Chemistry," http://www.doc88.com/p-66828838217.html. Wiley-VCH Venag GmbH & Co. KGaA. (727 pages).
Bowman, C.T. et al., "Optimization of Synthetic Oxygenated Fuels for Diesel Engines Investigators," GCEP Technical Report 2006. pp. 1-10.
Burak, S.R. "Homogenization—Improving Heavy Fuel Oil Usage by Homogenization," Ashland Specialty Chemical Company Drew Marine Division; Date is Unavailable. 9 pages.
Caldwell, T.A. et al., "Third Body Enhanced Methane Conversion in a Dielectric-Barrier Discharge Reactor"; University of Oklahoma. pp. 490-495. Date is unavailable.
Park, et al., "Electrostatic charging phenomenon in gas-liquid-solid flow systems," Chem. Eng. Sci. 62 (2007, pp. 371-386.
Environmental Effects EPA Chapter 1 External Combustion Sources, AP 42, Fifth Edition, vol. I; Chapter 1: External Combustion Sources: http://www.epa.gov.ttnchie1/ap42/ch01/. 12 pages.
Fayyad, S. et al., "Emulsfied Diesel Fuels in Engines: Experimental Emulsified Diesel and Benzen Investigation," Res. J. Appl. Sciences, Eng. Tech., vol. 2(3): 268-273 (2010).
Feng, Z. and Anthony, R.G. "Reactions of Propane on Hydrous Metal Oxide-Supported Catalysts," Texas A&M University. pp. 1826-1832. Date is unavailable.
Fernando, S. and Hanna, M. "Phase Behavior of the Ethanolbiodiesel Diesel MicroEmulsion System," Transactions of the ASABE, vol. 48(3): 903-908 (2005).
Fu, G. et al., Mechanisms of Methane Activation and Transformation on Molybdenum Oxide Based Catalysts, J. Am. Chem., VI. 127(11): 3989-3996 (2005).
Fung, R. "The Upgrading of Heavy Oil Model Compounds Using Methane Activiated by Metal Oxides Encapsulated in Molecular Sieves," A Thesis submitted in conformity with the requirements for the degree of Master of Applied Science, Graduate Department of Chemical Engineering, University of Toronto (1999). 139 pages.
Harteck and Donde, "Reaction of Carbon Monoxide and Ozone," J. Chem. Phy., vol. 26: 1734 (4 pages) (1957).
Hong, K-S, et al., "Direct Water Splitting Through Vibrating Piezoelectric Microfibers in Water," J. Phys. Chem. Lett, vol. 1(6): 997-1002 (2010).
Ismagilov, Z. et al., "Direct Conversion of Methane on Mo/ZSM-5 catalysts to proceduce benzene and hydrogen: Achievements and perspectives," Energy Environ. Sci. (2008). pp. 526-541.
Johansen, T. & Schramm, J. et al., "Low-Temperature Miscibility of Ethanol-Gasoline-Water Blends in Flex Fuel Applications" International Combustion Engines Group, Dept. of Mechanical Engineering, Technial University of Denmar, Kgs. Lyngsby, Denmark. Energy Sources, Part A, 31: 1634-1645. 2009.
Kamimura, H. et al., "Upgrading of Bitumen with Supercritical Water for a System Combined with SAGD," Tohoku University, Japan, pp. 742-745. Date is unavailable.
Karimi, A. et al., "Catalytic Oxidative Coupling of Methane-Experimental Investigation and Optimization of Operational Conditions," Petroleum & Coal, vol. 49(3): 36-40 (2007).
Kesling, H.S. et al., "Oxygenated Microemulsion Diesel Fuel," ARCO Chem. Co. pp. 322-326. Date is unavailable.
Knothe, G. and Dunn, R.O., "Dependence of Oil Stability Index of Fatty Compounds on Their Structure and Concentration and Presence of Metals," JAOCS, vol. 80(10), 2003. pp. 1021-1026.
Larkin, D.W. et al., "Oxygen Pathways and Carbon Dioxide Utilization in Methane Partial Oxidization in Ambient Temperature Electric Discharges,", Energy & Fuels, vol. 12: 740-744 (1998).
Larkin, D.W. et al., "Production of Organic Oxygenates in the Partial Oxidation of Methane in a Silent Electric Discharge Reactor," Ind. Eng. Chem. Res., vol. 40: 1594-1601: 40 (2001).
Leite, L.F. et al., Survey of Microwave Technology Potential Application in Heavy Crude Oil Upgrading, 2nd Mercosur Congress on Chemical Engineering and 4th Mercosur Congress on Process Systems Engineering. 11 pages. Date is unavailable.
Lif, A. and Holmberg, K, "Water-in-diesel emulsions and related systems," Advances in Colloid and Interface Science, 1233-126 (2006) pp. 231-239.

(56) References Cited

OTHER PUBLICATIONS

Linde, N. et al., "Streaming current generation in two-phase flow conditions," Geophysical Research Letters, vol. 34: L03306 (Jan. 10, 2007). 8 pages.
Liu, C-J et al., "Converting of Carbon Dioxide Into More Valuable Chemicals Using Catalytic Plasmas," Tianjin University, China. pp. 694-697. Date is unavailable.
Liu, C. et al., "Methane Conversion to Higher Hydrocarbons in a Corona Discharge over Metal Oxide Catalysts with OH Groups," Appl. Catalysis, General 164: 21-33 (1997).
Loviat, F. "Photoassisted Activation of Methane Over Supported Catalysts with a Xenon Excimer Lamp," A dissertation submitted to Eth Zurich, Dissertation Eth No. 18145 (2009). 179 pages.
Maroni, P. "Bond and Mode Specific Reactivity of Methane on Ni(100)," Thesis No. 3335 (2005). 191 pages.
Marsden, S.S., "Two Phase Streaming Potentials," Proceedings, Twelfth Workshop on Geothermal Reservoir Engineering, Stanford University, Stanford, California Jan. 20-22, 1987. pp. 147-151.
Mohammad, A.A. et al., "Experimental Investigation of in situ Upgrading of Heavy OII by Using a Hydrogen Donor and Catalyst During Steam Injection," Aug. 2008. 199 pages.
Ng, F.T.T. "Upgrading Heavy Oilbitumen Emulsions Via in situ Hydrogen Generation," Date not listed. 5 pages.
Ohyama, R. et al., "Electrical Current Condition and Electrohydrodynamically induced fluid flow in an AW type EHD pump," J. of Electrostatics vol. 53(2) Aug. 2001, pp. 147-158.
Okajima, S. et al., "Discovery of Principle on Combustion Promotion by a Specific Wave Number at the Regime of Far Infrared Ray—The Challenge to Realization of High Energy Saving and Low Emission of Co2," http://www.combustion.org.uk/ECM_2009/P810032.pdf. 2009. 5 pages.
Ovalles, C. et al., "Upgrading of Extra-Heavy Crude Oil by Direct Use of Methane in the Presence of Water—Deuterium-Labelled Experiments and Mechanistic Considerations," Fuel 1995. vol. 74, No. 8. pp. 1162-1168.
Ovalles, C. et al., Upgrading of Extra-Heavy Crude Using Hydrogen Donor Under Steam Injection Conditions, Characterization by Pyrolysis GC-MS of the Asphaltenes and Effect of a Radical Initiator (Key Paper); Fuel Chem. Div. Preprints. 2003, 48(1), pp. 59-60.
Ovalles, C. et al., "Use of a Dispersed Iron Catalyst for Upgrading Extra-Heavy Crude Oil Methane as Source of Hydrogen," Universidad Central de Venezuela, Apdo. 47 102, Caracas 1040A, Venezuela. Fernando Gonzales-Giminez, B. Pierre Embaid, Depto. de Fisica, Ciencas, UCV, Apdo. 47586, Caracas 1041A, Venezuela. pp. 521-525. Date Not Listed.
Rahimi, P., et al., "The Use of Methane as Source of Higher Hydrocarbons and Hydrogen for Upgrading Heavy Oils and Bitumen," http://www.anl.gov/PCS/acsfueld/preprint%20archive/Files/43_3_Boston_08-98_0476.pdf. pp. 476-480. Date Not Listed.
Reppert, P.M. et al., "Frequency-Dependent Streaming Potentials," J. of Colloid and Interace Science, vol. 234: 194-203 (2001).
Roy, R. "The Structure of Liquid Water; Novel Insights from Materials Research; Potential Relevance to Homeopath," Materials Research Innovations Online. Sep. 2005. pp. 577-608.
Sasaki, T. et al., "Process Developments of Natural Gas Conversion Technology to Liquid Fuels Via OCM Reaciton New" http://www.anl.gov.PCS/acsfuel/preprint%20archive/Files/40_1_anaheim_04-95_0105.pdf. pp. 105-109. Date Not Listed.
Soulivong, D. et al., "Cross-Metathesis of Propane and Methane: A Catalytic Reaction of C_C Bond Cleavage of a High Alkane by Methane," Communications. Chem Int. Ed. 2004, pp. 5366-5369.
Watanabe, H. et al., "An Experimental Investigation of the Characteristics of the Secondary Atomization and Spray Combsion for Emulsified Fuel," J. Chem. Eng. Japan, vol. 41(12): 1110-1118 (2008).
Wey, A.C. et al., "Infrared-Excitation for Improved Hydrocarbon Fuel's Combustion Efficiency," 7APAC-45. 2007, pp. 1-8.
Yi, Y. et al., "Change of asphaltene and resin properties after catalytic aquathermolysis," Pet. Sci. (2009) 6: 194-200.
Yuan, Y. et al., "Dehydro-Aromatization of CH4 Over W/HZSM-5-Based Catalysts," Fuel Chem. Div. Preprints 2002, 47(1), pp. 307-308.
Zhao, L. et al., "A Numerical Model of a Wire-Plate Electrostatic Precipitator Under Electrohydrodynamic Flow Conditions," Dept. of Electrical and Computering Engineering, University of Western Ontario, London, Ontario Canada (Jun. 2006). pp. 1-9.
International Search Report issued for PCT/US2012/031239, dated Mar. 13, 2013 (2 pages).
"Low Temperature Plasma Science: Not Only the Fourth State of Matter but All of Them," Report of the Department of Energy Office of Fusion Energy Sciences, Workshop on Low Temperature Plasmas, Mar. 25-27, 2008 (52 pgs.).
Agiral, A., "Electron Driven Chemistry in Microreactors," Thesis, University of Twente, 172 pages, (2009).
Akishev, et al., "Self-Pulsing Regime of DC Electric Discharge in Dielectric Tube Filled With Water Containing Gas Bubble," Plasma Science, IEEE Transactions on , vol. 36, Issue 4, pp. 1142-1143 (Aug. 2008).
Babaeva, N.Y. and Kushner, M.J., "Branching and Structure of Streamers in Gases, Liquids and Gaseous Bubbles Immersed in Liquids," Department of Electrical Engineering & Computer Science, University of Michigan; Downloaded from http://uigelz.eecs.umich.edu/Projects/STREAMERS/Natalie_streamer_project_v02.html on Dec. 12, 2014;Last Updated Jun. 12, 2009 (3 pgs.).
Becker, et al., "Plasma-Assisted Reforming and Hydro-Desulfurization of Diesel Fuels for Fuel Cells," Polytech Institute of NYU, 18 pages. (undated).
Boodhoo, K., "Intensification of Gas-Liquid Mass Transfer Using Porous Impellers for Application to an E.Coli Batch Fermentation Process," PIN Meeting, Nov. 16, 2006 (20 pgs.).
Boumans, A.A., "Streaming Currents in Turbulent Flows and Metal Capillaries. III. Experiment (1). Aim and Procedure," Physica, vol. 23, Issue 6-10, pp. 1038-1046 (1957).
Ceccato, Paul, "Filamentary plasma discharge inside water: initiation and propagation of a plasma in a dense medium," Thesis (Dec. 16, 2009) (203 pgs.).
Chang, et al., "EHD Surface Waves of Diesel Oil Thin Films Generated by Wire-Plate Barrier Discharges," IEEE Annual Report, Conference on Electrical Insulation and Dielectric Phenomena, Minneapolis, Oct. 19-22, 1997 (pp. 664-667).
Choudhary, et al., "Low-Temperature Nonoxidative Activation of Methane over H-Galloaluminosilicate (MFI) Zeolite," Science, vol. 275, No. 5304, pp. 1286-1288 (Feb. 28, 1997).
Conde, et al., "Frequency Effects in the Catalytic Oligomerization of Methane Via Microwave Heating," Fuel Chemistry Division Preprints 2002, vol. 47, No. 1, pp. 273-277 (2002).
FIR Fuel Activator—Infrared Aldi Far-IR Products Slides; www.gefir.com/FIR_Fuel_Activator-71124.pps, undated (43 pgs.).
Goerz, Jr., David J., "Combined Oxidative, Methanated and Hydotreated Fuel Reaction Disclosure," dated Mar. 12, 2013 (1 pg.).
GreatPoint Energy Website, "Our Technology," Downloaded from http://www.greatpointenergy.com/ourtechnology.php on Dec. 12, 2014 (2 pgs.).
Guczi, et al., "Low-Temperature Coupling of Methane," Catal. Rev.-Sci. Eng., vol. 38, No. 2, pp. 249-296 (1996).
Harteck, P. and Dondes, S., "Reaction of Carbon Monoxide and Ozone," J. Chem. Phys., vol. 26, 1734-1737 (1957) (5 total pages).
Hong, et al., "Plasma Technology in Heavy Oil Processing," www.paper.edu.cn/index.php/default/releasepaper/paper_all/4409783; undated (6 pgs.).
Indarto, et al., "Kinetic Modeling of Plasma Methane Conversion in a Dielectric Barrier Discharge," vol. 89, Issue 2, pp. 214-219 (Feb. 2008).
Kado, et al., "Diagnosis of Atmospheric Pressure Low Temperature Plasma and Application to High Efficient Methane Conversion" Catalysis Today, vol. 89, pp. 47-55 (2004).
Kado, et al., "Reaction Mechanism of Methane Activation Using Non-Equilibrium Pulsed Discharge at Room Temperature," vol. 82, Issue 18, pp. 2291-2297 (Dec. 1, 2003).
Kaneko, et al., "Static Gas-Liquid Interfacial Direct Current Discharge Plasmas Using Ionic Liquid Cathode," J. Appl. Phys., vol. 105, 103306-103306-5 (2009) (6 total pages).

(56) References Cited

OTHER PUBLICATIONS

Kong, et al., "Plasma Processing of Hydrocarbon, Electric Power 2007," Idaho National Laboratory, May 2007 (12 pgs.).
Kong, et al., "Reactive Plasma Upgrade of Squalane—A Heavy Oil Simulant," International Symposium on Plasma Chemistry, vol. 2, pp. 607-612 (1996).
Kozlov, et al., "Synthesis of Organic Compounds From Mixtures of Methane With Carbon Dioxide in Dielectric-Barrier Discharges at Atmospheric Pressure," Plasmas and Polymers, vol. 5, No. 3/4, pp. 129-150 (2000).
Lane, Jim, "Anellotech and the Advent of the Green Enes," Downloaded from http://www.biofuelsdigest.com/bdigest/2013/03/10/anellotech-and-the-advent-of-the-green-enes/ on Mar. 10, 2013 (3 pgs.).
Liu, et al., "Catalytic Oxidative Desulfurization of a Model Diesel," Thesis, Louisiana State University and Agricultural and Mechanical College, Aug. 2010 (76 pgs.).
Liu, et al., "Kinetics and Mechanism of Plasma Oxidative Desulfurization in Liquid Phase," Energy & Fuels, vol. 15, pp. 38-43 (2001).
Mohammedi, et al., "Desulfurization Study of Hydrocarbon Molecules by Plasma Process for Gasoil Applications," (2005) Downloaded from https://web.anl.gov/PCS/acsfuel/preprint%20archive/Files/41_1_NEW%20ORLEANS_03-96_0503.pdf on Dec. 12, 2014, pp. 503-509.
Murphy, et al., "Functionalization and Fragmentation During Ambient Organic Aerosol Aging: Application of the 2-D Volatility Basis Set to Field Studies," Atmos. Chem. Phys., vol. 12, pp. 10797-10816 (2012).
Park, et al., "Electrostatic Charging Phenomenon in Gas-Liquid-Solid Flow Systems," vol. 62, Issues 1-2, Jan. 2007, pp. 371-386.
Park, et al., "Micro Bubble Formation on sub-mm Tip Electrode Discharge in the Electrolyte Solution," Downloaded from http://www.ispc-conference.org/ispcproc/papers/647.pdf on Dec. 12, 2014 (4 pgs.).
Pawelec, et al., "Towards Near Zero-Sulfur Liquid Fuels: A Perspective Review," Catal. Sci. Technol., vol. 1, pp. 23-42 (2011); Retraction published Dec. 3, 2012.
Plasma Science: Advancing Knowledge in the National Interest, Plasma 2010 Committee, Plasma Science Committee, National Research Council, ISBN: 0-309-10944-2, 280 pages, 7×10, (2007) (280 pgs.).
Pushkarev, et al., "Methane Conversion in Low-Temperature Plasma," High Energy Chemistry, vol. 43, No. 3, pp. 156-162 (Jan. 2009).
Rahimi, P.M. and Gentzis, T. *The Chemistry of Bitumen and Heavy Oil Processing*, National Centre for Upgrading Technology, Alberta, Canada; http://chentserver.uwaterloo.ca/aelkamel/che720/che735/lectures_che735_students/new-boo-practical-advances-refinery/chapter19-bitumen-and-heavy-oil-processing.pdf; 38 pgs. (undated).
Sarnobat, et al., "The Impact of External Electrostatic Fields on Gas-Liquid Bubbling Dynamics," vol. 59, Issue 1, pp. 247-258 (Jan. 2004).
Schellekens, et al., "Enhancements in the well to wheel path of natural gas," MDP Final Report, Nov. 2007 (68 pgs.).
Search Report issued by the Polish Patent Office in Corresponding Polish Application No. P-406629 mailed Apr. 29, 2004 (2 total pgs.—including translation).
Sprunt, et al., "Streaming potential from multiphase flow," Geophysics, May 1994, vol. 59, No. 5, pp. 707-711, published online May 1, 1994.
Sreethawong, T. et al., "Partial Oxidation of Methane with Air for Synthesis Gas Production in a Multistage Gliding Arc Discharge System", Chulalongkorn University; Available online Sep. 12, 2006. Int'l. J. Hydrogen Energy, 32 (2007). pp. 1067-1079.
Tachibana, K., "Microplasma Generation in Artificial Media and Its Potential Applications," Pure Appl. Chem., vol. 82, No. 6, pp. 1189-1199 (2010).
Thagard, et al., "The Production of Hydrogen and Olefin Hydrocarbons by Electrical Discharge in Liquid Fuels," Poster Session 1 (2009); Downloaded from http://www.electrostaticanswers.com/2009ESJC/Poster1/2009%20Mededovic%20Production%20of%-20Hydrogen%20and%20Olefin%20Hyddrocarbons.pdf on Dec. 12, 2014 (6 pgs.).
Urashima, K. and Chang, J. S., "Removal of volatile organic compounds from air streams and industrial flue gases by non-thermal plasma technology" IEEE Transactions on Dielectrics and Electrical Engineering, vol. 7, No. 5, pp. 602-614 (2000).
Xia, et al., "Removal of Ammonia From Gas Streams With Dielectric Barrier Discharge Plasmas" vol. 152, Issue 1, pp. 113-119 (2008).
Zhang, et al., "Research Advances in Oxidative Desulfurization Technologies for the Production of Low Sulfur Fuel Oils," Petroleum & Coal, vol. 51(3), pp. 196-207 (2009).
Zongxuan, et al., "Oxidative Desulfurization of Fuel Oils," Chin. J. Catal., vol. 32, pp. 707-715 (2011).
Extended European Search Report issued by the European Patent Office for European Patent Application No. 15151831.3 dated Mar. 30, 2015 (11 pages).

* cited by examiner

HYBRID FUEL AND METHOD OF MAKING THE SAME

CROSS-REFERENCE TO RELATED APPLICATIONS

This application claims the benefit under 35 U.S.C. §119(e) to U.S. Provisional Patent Application No. 61/469,036, entitled Hybrid Fuel and Method of Making the Same, filed on Mar. 29, 2011, the contents of which are incorporated in its entirety by reference herein.

FIELD OF INVENTION

This invention generally relates to the formulation and production of hybrid fuels, and, more specifically, to techniques for the production of liquid fuels, including mineral-, plant-, and animal-based hydrocarbons.

BACKGROUND

Transportable liquids are important commodities for fuel and chemical use. Currently, liquid hydrocarbons are mostly frequently produced from crude oil-based feedstocks by a variety of processes. However, as the world supplies of crude oil feedstocks decrease, there is a growing need to find alternative sources of liquid energy products. Possible alternate sources include biomass, coal and natural gas. Methane, which is the major constituent of natural gas, biogas and coal gasification is a source along with emulsions including vegetable and animal fats. World reserves of natural gas are constantly being upgraded and more natural gas is currently being discovered than oil.

Because of the problems associated with transportation of large volumes of natural gas, most of the natural gas produced along with oil, particularly at remote places, is flared and wasted. Hence the conversion of natural gas directly to higher hydrocarbons, is a particularly attractive method of upgrading natural gas, providing the attendant technical difficulties can be overcome. A large majority of the processes for converting methane to liquid hydrocarbons involve first conversion of the methane to synthesis gas ("syngas" as used herein), a blend of hydrogen and carbon monoxide. Production of synthesis gas is capital and energy intensive; therefore routes that do not require synthesis gas generation are preferred. For example, conventional hydrotreating utilizes two steps, first for production of syngas, and then creation of free radicals under high temperatures and pressure for reaction with oils to be hydrotreated. Such processes are very energy intensive. A number of alternative processes have been proposed for converting methane directly to higher hydrocarbons.

Existing proposals for the conversion of light gases such as methane and carbon dioxide, as well as biofuels, to liquid fuels suffer from a variety of problems that have limited their commercial potential. Oxidative coupling methods generally involve highly exothermic and potentially hazardous methane combustion reactions, frequently require expensive oxygen generation facilities, and produce large quantities of environmentally sensitive carbon oxides. On the other hand, existing reductive coupling techniques frequently have low selectivity to aromatics and may require expensive co-feeds to improve conversion and/or aromatics selectivity. Moreover, any reductive coupling process generates large quantities of hydrogen and, for economic viability, requires a route for effective utilization of the hydrogen byproduct. Since natural gas fields are frequently at remote locations, effective hydrogen utilization can present a substantial challenge.

Another key factor in hydrocarbon liquids is the presence of polynuclear aromatic compounds, as well as total aromatic compounds. In some instances, these compounds are known to be carcinogens. Regulatory agencies have begun to turn their attention to the prevalence of these compounds in the environment and are requiring the reduction of polynuclear aromatics in industrial processes, including fuel processing. Moreover, polynuclear aromatics have a tendency to produce fine particulates when they are combusted, leading to further environmental concerns. However, the reducing of polynuclear aromatic compounds is difficult with existing refining processes because of the variety, technical difficulty and expense of the different reaction pathways required for reduction of polynuclear aromatic compounds. For example, in certain situations, reduction of polynuclear aromatic compounds requires addition of significant quantified of hydrogen gas and results in generation of carbon dioxide, which in itself requires removal and/or remediation.

A particular difficulty in using natural gas as a liquid hydrocarbon source concerns the fact that many natural gas fields around the world contain large quantities, sometimes in excess of 50%, of carbon dioxide. Carbon dioxide is a target of increasing governmental regulation because of its potential contribution to global climate change. In addition, any process that requires separation and disposal of large quantities of carbon dioxide from natural gas is likely to be economically prohibitive. In fact, some natural gas fields have such high carbon dioxide levels as to be currently considered economically unrecoverable.

Similarly, the existing processes for the production of biofuels from fats and oils commonly utilize esterification for the production of Biodiesel, particularly in its unblended form (i.e., B100). This is a costly process, and there are known technical issues with utilizing the Biodiesel, particularly as B100, in existing installations. Embodiments of the invention described below address these issues.

There are also large reserves of heavy oil/bitumen that cannot be readily used. Economically reducing the viscosity (i.e., increasing the API gravity) of heavy oils increases their value to the refiner and also reduces the cost of transportation.

There is also a need to improve the performance of fuels for transportation and heating applications. These improvements include increased efficiency for conversion of the energy to useful work and reduction of emissions of Greenhouse Gases (GHG), including $CO_2$, hydrocarbons, $SO_X$, $NO_X$, and of particulates. Further still, there is need to reduce the aromatic fractions, including polycyclic aromatics, in hydrocarbon fuels and biofuels.

There is a need for an improved process for converting light gas (e.g., methane) to liquid hydrocarbons, particularly where the light gas is present in a natural gas stream containing large quantities of carbon dioxide. There is also a need to create a hybrid fuel to utilize the unique characteristics of products produced from natural gas, bio fats and oils, crude and heavy oil/bitumen in a blended fuel that can be produced at costs comparable with existing hydrocarbon fuels. There is a need for process integration, systems, and apparatus that reduce the total emissions of Greenhouse Gases (GHG) and particulates based on Life Cycle analysis.

Such processes also require the potential to utilize carbon dioxide to minimize the emissions thereof.

BRIEF SUMMARY OF THE INVENTION

The invention provides hybrid fuels and methods for making the same.

In one aspect, a hybrid fuel is disclosed that is prepared from a process that includes: introducing a first reactant to a reactor, where the first reactant includes one or more light gases; exposing the first reactant to non-thermal plasma under conditions sufficient to reform the first reactant to form syngas and to generate free radicals and energetic electrons; introducing a first liquid feed fuel to the reactor; and intimately contacting the reaction products from the exposure of the first reactant to non-thermal plasma with the first liquid feed fuel in the reactor to produce a modified liquid fuel. As disclosed herein, the hybrid fuel prepared in accordance with the disclosed processes is usable as a drop-in fuel. In certain embodiments, a blend or mixture is prepared with the hybrid fuels prepared in accordance with the invention. Such blends include, without limitation, biodiesel, biofuel emulsions, jet fuel, diesel, and other conventional fuel products as the other components to the mixture. In one embodiment, the first reactant further comprises a second liquid fuel feed.

In one aspect a hybrid fuel is provide the hybrid fuel includes a first fuel product and a second fuel product. The first fuel product includes, without limitation a biofuel emulsion, biodiesel, jet fuel, diesel, ultra-low-sulfur diesel or other petroleum based fuels (e.g., the result of 102 of FIG. 1 or 222 of FIG. 2). The second fuel product includes a fuel prepared from one or more light gases combined with a liquid fuel feed (e.g., 328 of FIG. 3B or the result of 104 of FIG. 11. In some embodiments, the hybrid fuel includes at least about 20% by weight of the first fuel product. In some embodiments, the hybrid fuel includes up to about 20% by weight of the first fuel product. In further embodiments, the hybrid fuel includes from about 5% to about 10% by weight of the first fuel product. In other embodiments, the hybrid fuel includes water. In some embodiments, the hybrid fuel includes about 20% by weight of the first fuel product and about 80% by weight of the second fuel product. In some embodiments the hybrid fuel further includes up to about 20%, or about 10% to about 20% or about 20% water, the balance of the composition including the second fuel product. In some embodiments, the pour point of the hybrid fuel is about −30° C. In other embodiments, the pour point of the hybrid fuel is less than about −15° C. In further embodiments, the pour point of the hybrid fuel is about −10° C. to about −50° C., or about −25° C. to about −35° C. In other embodiments, the cloud point of the hybrid fuel is about −44° C. In further embodiments, the cloud point of the hybrid fuel is no more than about −10° C., or is about −15° C. In some embodiments, the pour point of the hybrid fuel is about −10° C. to about −15° C., or about 15° C. lower than the pour point of the second fuel product in isolation (i.e., not in the presence of the first fuel product, or prior to combining to produce the hybrid fuel). In some embodiments, the hybrid fuel includes no more than about 1% polynuclear aromatics. In other embodiments, the hybrid fuel includes no more than about 20% aromatics. In some embodiments, the second fuel product is a hybrid fuel produced from the processes described herein. In some embodiments, the first fuel product also includes a glycerol ether.

In another aspect, a process for the preparation of a hybrid fuel is disclosed. The process includes: introducing a first reactant to a reactor, where the first reactant includes one or more light gases; exposing the first reactant to non-thermal plasma under conditions sufficient to generate syngas (i.e., $CO+H_2$) and free radicals; introducing a first liquid feed fuel to the reactor; and intimately contacting the synthetic gas and the free radicals generated from the first reactant with the first liquid feed fuel in the reactor to produce a modified liquid fuel. In some embodiments, the hybrid fuel is a biofuel. In some embodiments, the process is a process for the refining of oil. In some embodiments, the process of generating free radicals is not preceded by a process for disassociating the one or more light gases (i.e., the reaction products from the first reactant are directly intermingled with the first liquid feed fuel). In some embodiments, the reactor is a non-thermal plasma reactor. In some embodiments, the non-thermal plasma reactor is a gliding arc reactor, a micro-plasma generator, or a homogenizer. In some embodiments, the free radicals are generated by high shear, ultrasonic, cavitation, high energy mixing devices, or combinations thereof.

In some embodiments, the processes for preparing a hybrid fuel disclosed herein further include adding a catalyst in the reactor. In some embodiments, the catalyst is a metal catalyst, an organometallic catalyst, a nanosphere catalyst, a supported catalyst, a soluble catalyst, or a mixture of two or more. In some embodiments, the catalyst is an organomolybdenum compound.

In some embodiments, the processes for preparing a hybrid fuel disclosed herein forms fatty acid ethyl esters (FAEE) and glycerol as byproducts. In some embodiments, the glycerol byproduct is further reacted to form one or more glycerol ether products, which is added to the hybrid fuel.

In a further aspect, a process for reforming light gas is provided. The process includes reforming one or more light gases in the presence of non-thermal plasma under conditions sufficient to generate the formation of free radicals. In certain embodiments, the reforming step is one or more of dry reforming (i.e., reacting methane with carbon dioxide in a reactor such as a plasma reactor), steam reforming, partial oxidation, and formation of methyl radicals. In some embodiments, the step of reforming one or more light gases is preformed at a pressure of less than about 5 atm. In other embodiments, the process is conducted at a temperature from about 200° C. to about 500° C. In some embodiments, the reforming step is one or more of dry reforming, steam reforming, partial oxidation, and formation of methyl radicals.

In some embodiments, in the processes for preparing a hybrid fuel disclosed herein the light gas is methane, natural gas, or a mixture thereof.

In one aspect, an apparatus for the preparation of a hybrid fuel is disclosed. The apparatus includes a first inlet for introducing a first reactant, where the first reactant comprises one or more light gases; electrodes in fluid connection with the inlet, where the electrodes are capable of producing an arc upon application of voltage and wherein the electrodes define a path for passage of the first reactant; a second inlet for introducing a first liquid feed fuel to the apparatus; an exit zone in which the product of the reaction of the first reactant and the electrodes and the first liquid feed fuel comes into contact; and an outlet in fluid connection with the exit zone. In some embodiments, the exit zone is interposed between and in fluid communication with the path defined by the electrodes and the second inlet. In some embodiments, the apparatus also includes Helmholtz coils. In some embodiments, the Helmholtz coils are located in or near the reactor. In some embodiments, the Helmholtz coils are located in or near the exit zone.

In some embodiments, the apparatus further includes a catalyst. In some embodiments the catalyst is located in or near the exit zone.

In some embodiments, the apparatus further includes heating coils. In some embodiments, the heating coils are capable of heating the contents of the apparatus to a specified temperature.

In some embodiments, the apparatus further includes a low work force cathode. In some embodiments, the low work force cathode functions to increase electron flow and/or electron density. In some embodiments, the low work force cathode includes thorium.

In one aspect, a process for the conversion of light gases into liquids is provided. Exemplary processes are those that utilize the generation of free radicals for the conversion process. In some nonlimiting embodiments, the processes include utilizing non-thermal plasma. Non-thermal plasma is utilized to reform the light gases, i.e., to produce syngas ($H_2$ and CO), radicals, energetic electrons, or a mixture of two or more of these components. In certain embodiments, reactive intermediates generated in the plasma are converted directly to produce molecules of hydrocarbon fuels. Such embodiments provide for rapid transfer of exiting gases into liquid fuel feed, such as diesel or other suitable hydrocarbon liquid. Particular embodiments take advantage of the presence of the free radicals, which are short lived, and reacts them with a liquid fuel feed (e.g., in some embodiments, oil or a bio liquid) to hydrogenate the compounds present in the liquid fuel feed, thereby forming shorter chain molecules. In certain embodiments, utilizing a non-thermal plasma reactor has the advantage of maximizing the electron density in the reaction space.

In certain embodiments, the processes disclosed herein result in a reduction in the content of polynuclear aromatics and total aromatics in the hybrid fuel. For example, in some embodiments, the processes disclosed herein result in a concentration of polyaromatic compounds of less than about 5%, less than about 3%, less than about 2%, or less than about 1%, less than about 0.1% by weight. In some embodiments, the processes disclosed herein result in a concentration of aromatic compounds of less than about 35%, less than about 30%, less than about 25%, or less than about 20% by weight. In some embodiments, the processes disclosed herein result in a at least a two-fold, three-fold, five-fold, or ten-fold reduction in polyaromatic compounds relative to conventional processes. Additionally, the processes disclosed herein result in an increased volume of fuel product, relative to conventional fuel processes. Accordingly, the processes disclosed herein modify the molecular makeup of the components, resulting in a hybrid fuel that is relatively cleaner burning and having lower emissions of greenhouse gases and small particle smoke. Moreover, the processes disclosed here result in fuels with lower viscosity and pour points.

In the embodiments disclosed herein, the light gas includes, without limitation, methane, ethane, butane, $CO_2$, $H_2O$, and $H_2S$.

In certain embodiments, the biogas used in the processes disclosed herein contains up to about 40% $CO_2$. In some embodiments, the processes are useful for the treatment of heavy oils (e.g., sour crude) to lower the viscosity. The end products of the processes disclosed herein include heating oil, diesel, gasoline (petrol), marine and jet fuels.

In another aspect, processes for the reforming of methane and other lower hydrocarbons via the use of free radicals are disclosed. In some embodiments, the reforming processes have the advantage of producing reaction products that contain relatively low levels of aromatic compounds and polynuclear aromatic compounds. In particular embodiments, the processes disclosed herein result in a reduction in the formation of aromatic compounds and polynuclear aromatic compounds relative to conventional processes. In some nonlimiting embodiments, free radical generation is achieved through the use of non-thermal plasma.

In one aspect of the invention, a process for making a hybrid fuel is disclosed. The method includes the steps of combining a biofuel emulsion blend and a liquid fuel product to form a hybrid fuel. Optionally, the hybrid fuel can be combined with water in a water-in-oil process. Still further, and optionally, the hybrid fuel can be combined with oxygenate additives and additive packages.

In another aspect of the invention, a process for making a biofuel emulsion includes combining an oil and an alcohol, and, optionally, an emulsifier. The mixture is subjected to high pressure and then passed to an expansion chamber, which homogenizes the mixture. The mixture is then at least partially oxidized to produce a biofuel emulsion.

In a further aspect of the invention, a process for making a liquid fuel product includes combining a light gas and a liquid fuel feed, and, optionally, water, a catalyst, and an emulsifier into a mixture. The mixture is reacted in a reactor vessel to produce at least one modified fuel product in vapor form. The method can, optionally, include reacting the modified fuel vapor product in a gas phase catalytic reactor and condensing the vaporous product into a liquid fuel product.

In another aspect of the invention, a hybrid fuel is disclosed. Embodiments of the hybrid fuel include blends of biofuel emulsions and liquid fuel products. Implementations of the hybrid fuel can also be combined with water, oxygenate additive, and other additive packages.

In one aspect, the process described herein forms free-radicals as a result to supercritical homogenizer reaction, thus forming Fatty Acid Ethyl Esters (FAEE) and glycerol similar the products formed via conventional biodiesel processes. The glycerol can be removed and processed to ethers of glycerol, The ethers of glycerol can then be added to emulsion to lower the pour point and reduce the viscosity of the product.

Without wishing to be bound by a particular theory, it is speculated that the processes described herein for preparing hybrid fuels, including biofuels, are energy favorable. Moreover, test results have demonstrated an overall decrease in density of the hybrid fuel mixture, providing confirmatory evidence that the overall beneficial hydrogenation of aromatic compounds to hydrocarbons is occurring (i.e., the process successfully converts otherwise undesirable aromatics to useful fuel stock).

In one aspect, a process for producing feedstock is disclosed. The process includes: supplying carbonaceous feedstock to a hydromethanation reactor; and reacting the carbonaceous feedstock in the presence of a catalyst and steam to produce a plurality of gases. In some embodiments, the carbonaceous feedstock is coal, biomass, petroleum coke, or a mixture thereof. In some embodiments, the catalyst is an alkali metal. In some embodiments, the reacting step is performed under elevated temperature, pressure, or both.

BRIEF DESCRIPTION OF THE SEVERAL VIEWS OF THE DRAWINGS

For a more complete understanding of various embodiments of the present invention, reference is now made to the following descriptions taken in connection with the accompanying drawings in which.

DETAILED DESCRIPTION

Figure 1:
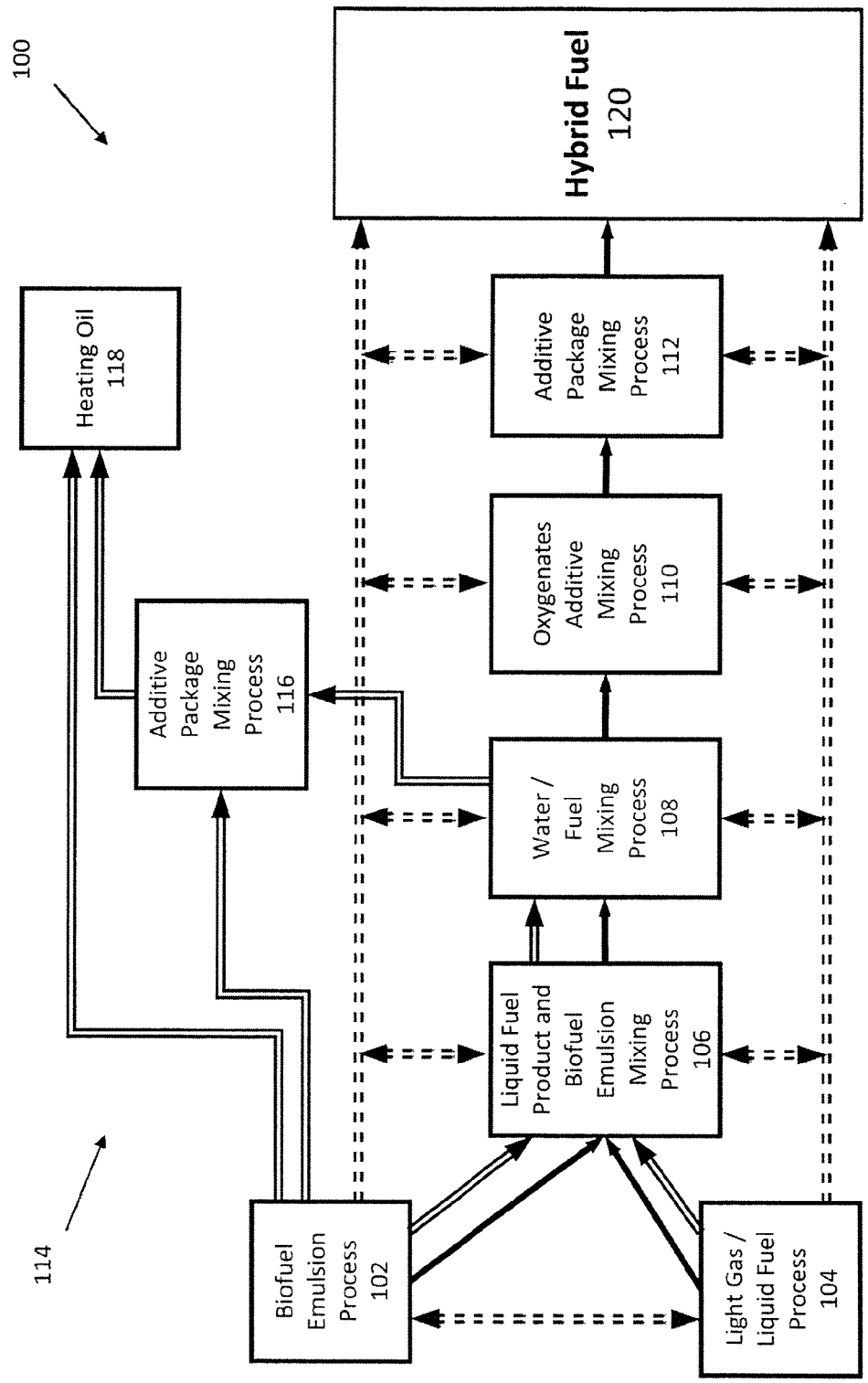
FIG. 1 illustrates an integrated process for producing a hybrid fuel according to one embodiment of the invention.

The term "biogas" is used herein to include any non-inert gas that can be produced by the biological degradation of organic matter. Non-limiting examples of biogas are hydrogen, methane, and carbon monoxide. Biogases, as used herein, also include other gaseous petroleum-based products such as ethane and ethylene, as well as decomposition products of agricultural waste such as wood chips, grains, grasses, leaves, and the like. The term "biogas" is also used herein to include the same gases that are obtained from other sources. One example is methane associated with coal, commonly known as "coal bed methane," "coal mine methane," and "abandoned mine methane." In some embodiments, such methane is derived by bacterial activity or by heating.

The term "natural gas", as used herein, is intended to mean a collection of materials that is formed primarily of methane, but it can also include ethane, propane, butane and pentane. The composition of natural gas can vary widely (e.g., varying from about 70%-100% or about 70% to about 90% methane, about 5%-15% ethane, and up to about 5% or up to about 20% propane or butane, individually or together), and it can include carbon dioxide, oxygen, water, nitrogen, hydrogen sulfide, an rare gases (e.g., argon, helium, neon, and xenon).

The term "light gas", as used herein, is intended to mean gases including carbon dioxide and hydrocarbons containing at least two carbons, such as methane, ethane, propane, ethanol, methanol, and mixtures of two or more thereof. In some embodiments, water is also included.

The term "biofuel", as used herein, generally refers to a liquid fuel that is made from animal, plant, and/or biological materials.

Under one aspect of the invention, hybrid fuels and methods of making the same are disclosed. The term "hybrid fuels", as used herein, generally refers to any one of many possible fuel formulations or blends, including "drop-in" fuel formations that use any one or more of readily available light gases (described in more detail below), hydrocarbon fractions, biofuels, water, and various additive packages. In some embodiments, hybrid fuels include the fuel product resulting from the combination of a light gas and a liquid fuel feed (e.g., natural gas and diesel). A drop-in fuel is one that is interchangeable and compatible with the conventional fuel it replaces. A drop-in fuel does not require adaptation of the heating system, burner system, engine or jet fuel system or modification of the fuel distribution network in which it is used. A drop-in fuel can be used "as is" or can be blended with the conventional fuel the drop-in fuel replaces.

"Energetic electrons" as used herein refer to electrons having elevated electron energy, such that they are able to participate in the decomposition of gaseous molecules (e.g., decomposition of methane or natural gas by disassociation or ionization). Energetic electrons are part of the processes disclosed herein (including without limitation the use of non-thermal plasma) that enable otherwise thermodynamically unfavorable reactions to occur. In some nonlimiting embodiments, energetic electrons have electron energy of about 1-10 eV, or greater than about 5 eV, or great than about 6.5 eV or even greater than about 10 eV. In some embodiments, a sufficient number of energetic electrons, or high-energy electrons, are involved with a phenomenon called electron avalanche, wherein secondary electrons are generated. In certain situations, the fragmentation pattern on radicals formed from methane is dependent in part of the electron energy distribution function (EEDF).

Embodiments of the processes for making hybrid fuels are flexible, fully integrated, and can be readily adapted to the available feedstocks on-hand as well as adapted to the type of hybrid fuel desired. For example, embodiments of the process can be adapted to produce drop-in replacements for any one or more of heating oil, diesel, gasoline, marine fuel, and jet fuel (e.g., Jet A, JP-8, JP-5, etc.). Similarly, embodiments of the process can be adapted to accept varying feedstocks, such as, plant oils, animal-derived fats, alcohols, natural gas, $CO_2$, heavy oils, diesel, biodiesel, and products from the gasification of biomass, coal, coke, and other materials. The integrated processes disclosed herein provide flexible operations that maximize economics of fuel availability and meet the requirements of multiple fuel uses including heating, transportation (e.g., vehicle, marine, jet, etc.) requirements. The processes disclosed herein are applicable to a large number of locations, including remote locations with limited natural gas reserves, and are suitable for moving equipment by truck or barge. Moreover, the processes have relatively low utility consumption (e.g., water) and involve relatively lower capital cost to implement.

As mentioned above and described in greater detail below, embodiments of the invention provide highly integrated processes for the production of hybrid fuels. A highly integrated plant is less sensitive to feedstock price and availability because many of the feedstocks for the individual processes are "internally supplied". That is, the primary or side-products of one sub-process feed the other sub-processes. Thus, a fewer number of feedstocks must be brought in from outside the process, which reduces the overall exposure to feedstock supply volatility.

Furthermore, the performance of the overall process is enhanced by a high degree of process integration. The flexibility of a highly integrated process enables the order of processing of the sub-processes to be changed to accommodate available feedstocks and desired hybrid fuel products. Similarly, the process can adapt to changing product demand and product economics by accommodating the manufacture of alternate hybrid fuel products. Environmental performance, too, is enhanced because by-products of certain sub-processes that would otherwise require disposal can be used as feedstocks for other sub-processes. This also reduces the costs of operation because disposal costs are avoided as well as the cost of the feedstocks themselves. Further still, in many cases, the capital expenditure for the entire integrated plant is lower than what would be incurred if the individual sub-processes were built independently. Likewise, transportation costs that would be incurred by shipping materials from one sub-process to another are avoided in an integrated process.

In one aspect, the processes disclosed herein include the formation of free radicals from light gases and utilizing the free-radicals in subsequent processes for the production of hybrid fuels. The processes disclosed herein demonstrate an advantage over conventional processes that require two distinct steps—a first step of disassociating a light gas and a second, subsequent step, of again creating free radicals at high temperatures and pressures to initiate further processing steps. The processes disclosed herein limit the need for these two distinct steps, thereby providing significant advantages (such as lower energy consumption) to the refiner and user. In exemplary embodiments disclosed herein, free radicals generated in the initial step are directly utilized in processes for the refining of oil and other fuel feed liquids. Moreover, the free radicals are available for use in other processes. The processes disclosed herein incorporate intimate (i.e., near term) contact with free radicals of the vapor phase and the subsequent liquid fuel feed (e.g., liquid or oil liquid phase) within the time of the existence of the free radical.

In another aspect, free radicals containing carbon, hydrogen, oxygen, or a mixture of two or more of carbon, hydrogen, and oxygen are created in processes for the reforming of light gases. In some embodiments, the reforming process is dry reforming ($CO_2+CH_4$), steam reforming, partial oxidation, or the formation of methyl radicals. In some embodiments, the process of reforming light gases is conducted in the presence of non-thermal (non-equilibrium) plasma. In some embodiments, the process of reforming light gases using non-thermal plasma is conducted at atmospheric pressure. In other embodiments, the process of reforming light gases using non-thermal plasma is conducted above atmospheric pressure. For example, in some embodiments, the process is performed at a pressure ranging from about 0.1 atm to about 5 atm. In some embodiments, the process is performed at a pressure up to about 5 atm. In some embodiments, the process is performed at pressure of about 100 Torr. In other embodiments, the reforming process is conducted under high shear conditions caused by ultrasonic excitation, spinning disks, homogenization, UV light sources, radiation, or a combination of two or more of these processes. In some embodiments, the radiation is electron radiation or particle (gamma) radiation or a combination thereof. In one embodiment, the source of radiation is thorium.

In conventional high temperature—high pressure processes, free radicals are formed during the reforming process, The claim is that the free radicals can be formed using a non-thermal (non-equilibrium) plasma. The energy consumption is lower. In a similar manner, the subsequent hydro processing of the liquids occurring at high temperature results in the formation of free radicals leading to chain reactions. The claim is that bringing the syngas with free radicals back to neutral and then recreating the free radical state is energy inefficient. The process utilizes the free radicals formed during the plasma operation to cause the continuing chain reactions. Similarly, the processes using the noon-thermal reactor likewise return the syngas or methyl radical back to normal condition.

In some embodiments, the processes disclosed herein include the use of catalysts. Such catalysts facilitate the gas shift reaction, as well as the rearrangement of the hydrocarbons. Exemplary catalysts include, without limitation, metals, nanospheres, wires, supported catalysts, and soluble catalysts. For example, as used herein, "nanosphere" or "nanocatalyst" refers to a catalyst in which the mean average diameter of the catalyst is in the range of 1 nm to 1 μm. In some embodiments, the catalyst is an oil soluble catalyst (also known as nanocatalysts). Such catalysts disperse well and do not precipitate during oil processing. In some embodiments, the catalysts is a bifunctional catalyst, for example one that includes an inorganic base and a catalyst containing a transition metal such as iron, chromium, molybdenum, or cobalt. In certain embodiments, catalysts are present in the reaction process at levels of about 0.03% to about 15% by weight. In some embodiments, the catalyst is present at a level of about 1%. In one nonlimiting exemplary embodiment, the concentration of soluble catalyst introduced into the reactant mixture falls is about 50 ppm, or about 100 ppm, or ranging from about 50 ppm to about 100 ppm of liquid oil. In some embodiments, the catalyst is present at a level of at least about 50 ppm. In some embodiments, the catalyst is present at a level ranging from about 50 ppm to about 100 ppm. In some embodiments, the catalyst is present at a level ranging In some embodiments, the catalyst is an organometallic compound. Exemplary organometallic compounds contain a transition metala transition metal-containing compound, or mixtures thereof. Exemplary transition metals included in catalyst compounds include catalysts selected from the Group V, VI and VIII elements in the Periodic Table of Elements. In certain embodiments, the transition metal of the catalysts is one or more of vanadium, molybdenum, iron, cobalt, nickel, aluminum, chromium, tungsten, manganese. In some embodiments, the catalyst is a metal naphthanate, an ethyl sulfate, or an ammonium salt of polymetal anions. In one embodiment, the catalyst is an organomolybdenum complex (e.g., MOLYVAWM 855 (R.T. Vanderbilt Company, Inc. of Norwalk, Conn., CAS Reg. No. 64742-52-5), an organomolybdenum complex of organic amide containing about 7% to about 15% molybdenum. In another embodiment, the catalysts is HEX-CEM (Mooney Chemicals, Inc., Cleveland, Ohio, containing about 15% molybdenum 2-ethylhexanote) or bimetallic wire, shavings or powder catalyst that is H25/L605 (Altemp Alloys, Orange Calif.) that includes about 50-51% cobalt, 20% chromium, about 15% tungsten, about 10% nickel, up to about 3% iron, and 1.5% manganese.

In further embodiments, other suitable catalysts include compounds that that are highly soluble in oil while having a relatively high loading of molybdenum. In some embodiments, the catalyst imparts lubricity to the fuel, which is necessary for ultra-low-sulfur diesel products (ULSDs), which. In some embodiments, the organometallic compound adds lubricity to the liquid fuel product, as well as serving as a catalyst, thereby avoiding the need to add further lubricity additives to the final hybrid fuel product. Other organometallic compounds that are useful for the processes disclosed herein are those disclosed in U.S. Pat. No. 7,790,018 to Khan, et al. and U.S. Pat. No. 4,248,720 to Coupland et al.

In some embodiments, the transition metal catalyst is a single transition metal or a combination of transition metals, either as metal salts, pure metals, or metal alloys, and, in some embodiments is used in combination with metals other than transition metals. Preferred catalysts for use in this invention are metals and metal alloys. In some embodiments, transition metals having atomic numbers ranging from 23 to 79 are employed; in other embodiments, those with atomic numbers ranging from 24 to 74 are more employed. In some embodiments, cobalt, nickel, tungsten, iron, and combinations thereof are employed as metals for catalyst compounds. A nonlimiting example of an additional metal that can be included is aluminum. In some embodiments, the transition metal(s), together with other metals such as aluminum are supported an iron frame. In some embodiments, the metal frame is a basket or in a bed. In some embodiments, the catalyst is deposited onto the surface of the electrode. A variety of forms of iron can be used as the frame material. Nonlimiting examples are pig iron, gray iron, and ductile iron. In certain embodiments, the metal windings are supported on the iron frame in the form of an open-mesh network, For example, in some embodiments. Gray iron castings include, for example, total carbon, 2.75 to 4.00 percent; silicon, 0.75 to 3.00 percent; manganese, 0.25 to 1.50 percent; sulfur, 0.02 to 0.20 percent; and phosphorus, 0.02 to 0.75 percent. Moreover, in some embodiments, one or more of the following alloying elements are present in varying amounts: molybdenum, copper, nickel, vanadium, titanium, tin, antimony, and chromium. In some embodiments, nitrogen is generally present in the range of about 20 to about 92 ppm.

The rate and extent of chemical reactions are limited by the laws of kinetics and thermodynamics. The rate of reaction is dependent on many things, including time, temperature, and pressure. In the case of catalyzed reactions there is the additional rate limiting factor of the contact time of the reactants with the catalyst and the time for reacted products to be removed from the surface of the catalyst to enable the catalyst to catalyze further reactants.

In some embodiments, the process to combine light gas with a liquid fuel feed is operated at temperatures from about 100° C. to about 850° C. In some embodiments, the process is performed at room temperature. In some embodiments, the process is performed at temperatures from about 200° C. to about 500° C., or about 500° C. to about 700° C. or about 700° C. to 850° C. In other embodiments, the process is performed at temperatures from about 300° C. to about 500° C. In some embodiments, the gases and liquid fuel feed are heated. The temperature is controlled to assist in the reaction process.

In some embodiments, the process is performed at pressure above 1 atm. In some embodiments, the process is performed at atmospheric pressure. In certain embodiments, the process is performed at positive pressure ranging from about 0.1 atm to about 5 atm. In some embodiments, the process is performed at pressure of no more than about 5 atm. In certain embodiments (e.g., microplasma reactors), the process is performed at pressures of up to about 100 Torr. In some embodiments, the pressure ranges from about 1200 psi to about 3000 psi.

In some embodiments, the process for producing a biofuel from a combination of a light gas and a liquid fuel feed is a liquid/gas or a vapor/gas phase process.

In some embodiments, the apparatus for reforming natural gas or for producing a biofuel is a non-thermal plasma reactor. Nonlimiting examples of non-thermal plasma reactors include gliding arc, vortex arc, distributed discharge, micro channel discharge, and dielectric barrier. In some embodiments, the apparatus or reactor includes a radiation source. Exemplary radiation sources include, without limitation, thorium. In some embodiments, the apparatus or reactor includes low work force materials to increase electron flow. In some embodiments, the apparatus or reactor includes a magnetic field.

The apparatus for producing free radicals includes, without limitation, non-thermal plasma reactors, high shear reactors, electron or particle beam reactors, and hybrid systems. Non-thermal plasma reactors include those in which electrons are activated and free radicals form under relatively low temperature conditions. In some embodiments, non-thermal plasma reactors utilize and external electrical source to create electric fields. The applied voltage is, in some embodiments, DC, while in other embodiments it is high frequency. Exemplary non-thermal plasma reactors include, without limitation, Gliding Arc reactors, microplasma reactors, homogenizers, high shear reactors. In further nonlimiting embodiments, non-thermal plasma reactors include vortex generators, micro-plasma generators, rotating disk with centrifugation, high frequency, microwave, and sonic activation. Nonlimiting examples of high shear reactors are homogenizer reactors, ultrasonic reactors, cavitation reactors, high energy mixing devices, and catalytic centrifugation reactors. Exemplary electron or particle beam free radical generators include, without limitation, high energy electron generators and radioactive sources. For example, in one embodiment, the radioactive source is a material that generates alpha particles, such as thorium.

In some embodiments, the reactors are microplasma reactors. Microplasmas are plasma reactors in sub-millimeter geometry. They possess high electron densities and a relatively high fraction of energetic (>20 eV) electrons which are theoretically able to efficiently promote chemical reactions. The microplasma reactors utilized herein operate with a non-thermal plasma and are ignited using either a direct current or pulsed DC power supply (<80 kHz). In one particular embodiment, the device is a microhollow cathode discharge (MHCD) with an elongated trench.

The use of microplasma technology to create the radicals from the reforming of natural gas provides higher electron and free radical densities, which should theoretically increase the overall efficiency. Plasma confined to at least one dimension 1 mm or less defines a microplasma. Microplasmas have much higher power densities (exceeding 1 kW/cm$^3$), higher electron densities (exceeding $10^{15}$ cm$^{-3}$) and increased surface-to-volume ratios when compared to conventional, large-scale plasma-chemical systems. A high surface-to-volume ratio imparts excellent thermal management and mixing characteristics that help maintain homogeneous, isothermal reacting volumes. These microplasma characteristics present processing advantages for hydrocarbon reforming applications. Operating at close to atmospheric pressure minimizes equipment requirements and simplifies the overall operating system.

In conventional reactors, contact time for the reactants and catalyst is often controlled by mixing which provides contact between components involved in a chemical reaction. There have been various innovations directed towards maximizing the use of mixing and mixing devices to accelerate chemical reactions. High shear and high energy mixing devices have been proposed for enhancing the rate of chemical reactions. There have been other devices proposed for accelerating the reactions of chemical reactants. For example, hydrodynamic cavitation has been proposed as a method of accelerating chemical reactions. Hydrodynamic cavitation involves phase change and rapid increases in temperatures and pressures; pressure variation caused by the variation in the flowing liquid velocity results in accelerated chemical reaction.

In general, high shear reactor is also be referred to as an emulsifier mixer, dispersion mixer, or sonic unit. Implementation of a specific reactor and process will include consideration of, among other things, the scale, cost, quality and quantity of feedstock. Homogenizer reactors are one type of configuration useful for the processes disclosed herein.

Without wishing to be limited to a particular theory, it is believed that the level or degree of high shear mixing is sufficient to increase rates of mass transfer and may produce localized, non-ideal conditions that enable reactions to occur that would not otherwise be expected to occur based on Gibbs free energy predictions. Localized, non-ideal conditions are believed to occur within the high shear device resulting in increased temperatures and pressures with the most significant increase believed to be in localized pressures. The increase in pressures and temperatures within the high shear device are instantaneous and localized and quickly revert to bulk or average system conditions once exiting the high shear device. In some cases, the high shear-mixing device induces cavitations of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid microcirculation (acoustic streaming). An overview of the application of the cavitation phenomenon in chemical/physical processing applications is provided by Gogate et a!., "Cavitation: A technology on the horizon," *Current Science* 91 (No. 1): 35-46 (2006). The high shear mixing device of certain embodiments of the present system and methods is operated under what are believed to be cavitation conditions effective to dissociate the reactants for the optimization of reactions. In certain instances, the conditions are effective for mechanically disintegrating and/or extracting hydrocarbons. Further, the conditions may be effective for mechanically homogenizing the hydrocarbon chains to produce liquid hydrocarbon products.

In some embodiment, tip speed, and therefore shear rate, is an important factor in achieving fine micro-emulsions. In one particular embodiment, SUPER DISPAX REACTOR combines extremely high shear rates with a fine generator geometry to produce high energy dispersions. Due to the high tip speeds, two stages are often all that is needed to achieve the results that are desired. In some embodiments, tip speeds exceeding 10,000 fpm are achieved.

High shear devices (HSD) such as high shear mixers and high shear mills, are generally divided into classes based upon their ability to mix fluids. Mixing is the process of reducing the size of in homogeneous species or particles within the fluid. One metric for the degree or thoroughness of mixing is the energy density per unit volume that the mixing device generates to disrupt the fluid. The classes are distinguished based on delivered energy density. There are three classes of industrial mixers having sufficient energy density to consistently produce mixtures or emulsions with particle or bubble sizes in the range of 0 to 50 flm.

Homogenization valve systems are typically classified as high-energy devices. Fluid to be processed is pumped under very high pressure through a narrow-gap valve into a lower pressure environment. The pressure gradients across the valve and the resulting turbulence and cavitations act to break-up any particles in the fluid. In some embodiments, these valve systems yield average particle size range from about 0.01 flm to about 1 flm. At the other end of the spectrum are high shear mixer systems classified as low energy devices. These systems usually have paddles or fluid rotors that turn at high speed in a reservoir of fluid to be processed, which in many of the more common applications is a food product. These systems are usually used when average particle, globule, or bubble, sizes of greater than 20 microns are acceptable in the processed fluid.

In some embodiments of non-thermal plasma reactors, a heterogeneous medium of the heavy hydrocarbon with a hydrogen-containing gas (e.g., syngas) in a chamber is exposed to both an electronic beam and an electric discharge field at the same time so as to create a thermal non-equilibrium as well as a spatially non-uniform state for this medium. Such dual exposure allows the cracking method to proceed without high temperature and high pressure typically required therefore and thus reduces the energy consumption and impurities generated along with desirable output product.

In other embodiments, a non-self sustaining electric discharge occurs by an external ionizer of a very high intensity, such as an Electron Beam (EB). An electric field of high intensity superimposed on the gas that, in turn, is exposed to the EB multiplies a number of electrons generated due to EB, and creates an electric discharge, which generates chemically active particles. Numerous applications of these discharges in homogeneous media are well known (e.g., for activating gas lasers). For example, chemical activity of an electric discharge supported by EB in a homogeneous gas is described in Y N Novoselov, V V Ryzhov, A I Suslov// Letters in Journal of Theoretical Physics, 1998. v. 24. No. 19; p. 41.

Similarly, the injection of gamma rays into the non-thermal plasma zone containing the gases causes is believed to improve the stability of the plasma and facilitate the initiation of the formation of free radicals. The 4 MEV gamma rays can be generated from emissions from thorium containing materials.

FIG. 1 shows an overview of an integrated process 100 for producing a hybrid fuel 120 according to one embodiment of the invention. Process 100 includes a variety of sub-processes, each of which is described in greater detail below. FIG. 1 presents an illustrative order in which the sub-processes can occur (shown by solid single lines). However, process 100 is flexible, and the order of the sub-processes may be varied according the particular feedstocks used and hybrid fuel 120 desired. In fact, in some implementations, one or more of the sub-processes may be omitted. This aspect is represented in broken double lines. FIG. 1 also shows an illustrative implementation of the process 100 for producing a drop-in replacement for heating oil 118, described in more detail below (shown in solid double lines).

Process 100 includes a biofuel emulsion process 102 for producing a biofuel emulsion product (described in more detail below) and a liquid fuel process 104 for producing a liquid fuel product (described in more detail below). Process 100 also includes a mixing process 106 in which the liquid fuel product is mixed with the biofuel emulsion. Process 100 further includes a water/fuel mixing process 108 for creating an emulsion of water and oil based using the biofuel emulsion, the liquid fuel, and/or mixture product of the two. Process 100 still further includes an oxygenates additive mixing process 110 for adding oxygenates to any of the intermediate products produced in process 100. Process 100 also includes an additive package mixing process 112 for adding various additive packages according to the feedstocks used and/or the hybrid fuel 120 desired. The additive packages are described in more detail below.

As mentioned above, an illustrative implementation of process 100 includes a process 114 for producing a heating oil product 118. In one embodiment, the product of the biofuel emulsion process 102 is directly used as the heating oil product 118. In another embodiment (not shown), approximately 5-20%, or in some embodiments about 10%, of the biofuel emulsion is blended with petroleum-based diesel to make a transport fuel. In yet another embodiment, the biofuel emulsion product is fed to additive package mixing process 116 to produce the heating oil product 118. Additive package mixing process 116 can be identical to process 112; it is shown separately here for the sake of clarity of illustration. Further still, a biofuel emulsion intermediate product from process 102 and a liquid fuel intermediate product from process 104 can be combined in mixing process 106, then further combined with water in process 108 before being combined with an additive package in process 116 to produce the heating oil product 118. As mentioned above, process 114 is merely illustrative of the flexibility of integrated process 100, and other sub-process combinations are within the scope of the invention.

Figure 2:
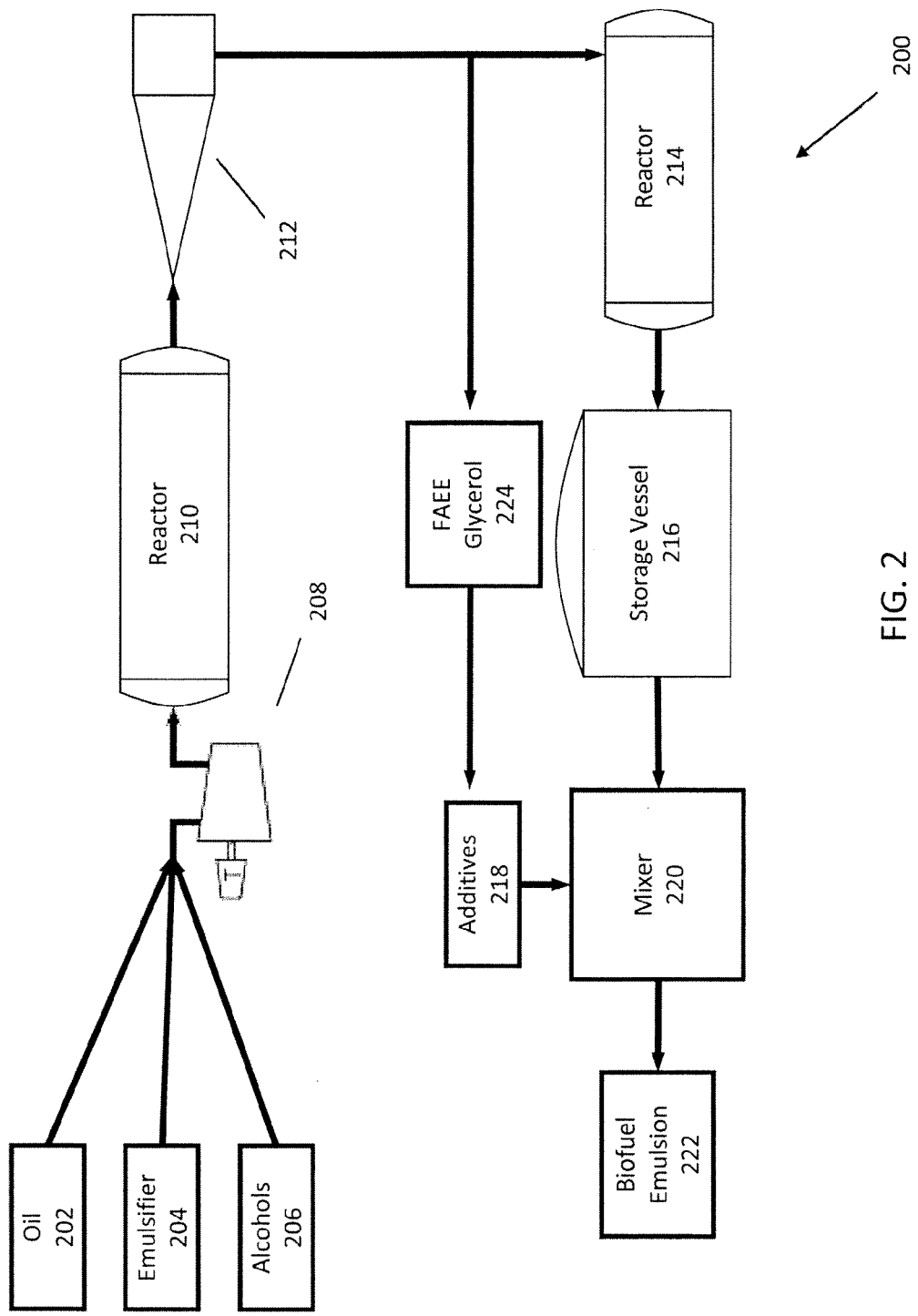
FIG. 2 illustrates a process for producing a biofuel emulsion according to one embodiment of the invention.

FIG. 2 is an overview of a biofuel emulsion process 200. In embodiments of integrated process 100, process 200 can be used as the biofuel emulsion process 102. Process 200 feeds an oil 202, an emulsifier 204, and an alcohol 206 to a centrifugal compressor 208, which performs some mixing of the feeds and increases the pressure of the mixture for supply to a reactor 210. In some implementations, the reactor 210 is a supercritical reactor, which subjects the mixture to high pressure (e.g., up to about 8000 psi). The intermediate product from the reactor 210 is then fed to an expansion vessel 212. The expansion vessel drops the pressure of the mixture as the mixture is impinged on a plate to provide a high degree of mixing and homogenization, and causes the mixture components to be broken-up into small particles (in some embodiments on the order of hundreds of nanometers), thereby promoting the formation of a stable emulsion.

In some alternative embodiments, fatty acid ethyl esters (FAEE) and glycerol 224 are generated as byproducts of process 200. In certain embodiments, the glycerol is further processed to glycol ethers, which can be added back into process 200 as additives (e.g., 218). Used as additives, glycol ethers reduce viscosity and pour point of the resulting biofuel emulsion 222. It is theorized that the action of the supercritical pressure from reactor 210 and rapid expansion creates a high shear environment that results in the formation of free radicals which then participate in the formation of FAEE and glycerol. Accordingly, the fuels containing FAEE and glycerol have increased heating value. Moreover, the inclusion of hydrous ethanol in the fuels described herein allows for the existence of stable water in the product and additional water content.

The emulsified intermediate product is passed through an oxidizing reactor 214. In some implementations, an oxygen containing gas is bubbled through the emulsified intermediate product, which may, optionally, occur at elevated temperatures. In so doing, it is believed that components in the emulsified intermediate products are oxidized (e.g., ethanol). By oxidizing at least a portion of the emulsified intermediate product, reactor 214 increases the flash point of the final biofuel emulsion 222. The oxidized intermediate product can be held in a storage vessel 216 for treatment with an additive package 218 via additive mixer 220 to produce the biofuel emulsion produce 222. The additive package addition is optional and is omitted in certain implementations. In some embodiments, the additive package includes oxidation stabilizers to reduce the rate of rancidity of biofuel produced from non-mineral crude oil feedstocks. As noted above, in some embodiments, the additive package also includes glycol ethers.

In some embodiments, the oil 202 used as a feedstock for process 200 includes plant oils, animal fats, and/or oils produced by hydrous pyrolysis (e.g., thermal depolymerization). Thus, illustrative examples of sources include Camelina, palm, soy, corn, rapeseed, Jatropha, and animal fats and wastes from various livestock farming operations. In certain embodiments, the alcohol 206 is any one of a mono-, di-, tri-, polyhydric alcohol, and/or a C1 to C4 alcohol. Meanwhile, exemplary emulsifiers 204 include, without limitation, any one or more of the various types of surfactants such as nonionic, ionic or partially ionic, anionic, amphoteric, cationic and zwitterionic surfactants. For example, any of the surfactants tabulated in U.S. Pat. Pub. No. 2010/0037513, entitled Biofuel Composition and Method of Producing a Biofuel, filed Sep. 18, 2009 (incorporated in its entirety by reference herein) can be used as emulsifier 204.

In one illustrative implementation of process 100, the techniques disclosed in U.S. Pat. Pub. No. 2009/0185963, entitled Method for Making Diesel Fuel Additive, filed Jan. 22, 2009, (incorporated in its entirety by reference herein) are used for process 200.

In another illustrative implementation of process 100, the techniques disclosed in U.S. Pat. Pub. No. 2010/0186288, entitled Method for Production of Emulsion Fuel and Apparatus for Production of the Fuel, filed Aug. 31, 2007, (incorporated in its entirety by reference herein) are used for process 200.

In yet another illustrative implementation of process 100, the techniques disclosed in U.S. Pat. No. 4,526,586, entitled Microemulsions From Vegetable Oil And Aqueous Alcohol With 1-Butanol Surfactant As Alternative Fuel For Diesel Engines, filed Sep. 24, 1982, (incorporated in its entirety by reference herein) are used for process 200.

Figure 3A:
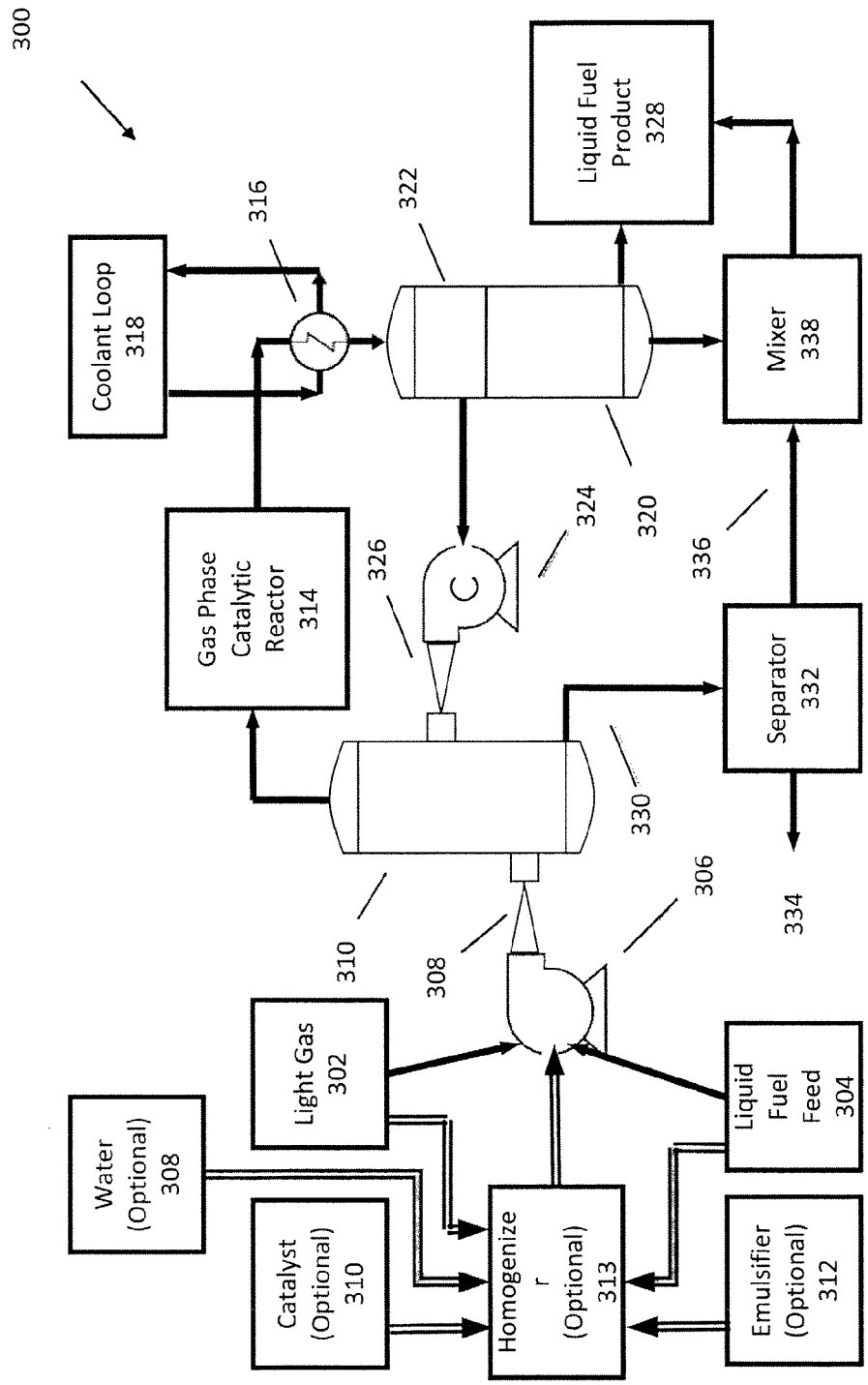
FIG. 3A illustrates a process for producing a liquid fuel product according to one embodiment of the invention.

FIG. 3A shows an overview of a process 300 for producing a liquid fuel product 328. In embodiments of integrated process 100, process 300 can be used as the liquid fuel process 104. A light gas 302 and a liquid fuel feed 304 are fed via a pump and/or compressor 306 through an ejector 308 to a reactor vessel 310 (as shown by solid lines). Optionally, the light gas 302 and liquid fuel feed 304 can be fed along with water 308 (which can be treated to have a negative oxidation/reduction potential (ORP) in the range of about −100 eV to about −500 eV), a catalyst 311, and/or an emulsifier 312 to pump/compressor 306 (shown by double lines) via a homogenizer 313. In some embodiments, air is also added in the process, through pump/compressor 306. The pump/compressor 306 and/or homogenizer 313 increases the homogeneity of the mixture before passing it through the ejector 308. The pump/compressor 306 can include a high shear centrifugal pump that assists in reducing the size of the droplets of individual components of the mixture. Moreover, the ejector 308 aids in the production of small bubbles and/or fluid droplets (depending on the phase of the component) that increases the reactivity of the components of the mixture by increasing overall contact between the components.

Although not shown, all of the components that can be feed to the homogenizer 313 can be fed directly to the pump 306 while the liquid fuel feed 304 passes through the homogenizer 313 before entering the pump 306. In such an implementation, the homogenizer breaks-up the liquid fuel feed 304 (which could include, e.g., heavy oil, bitumen, and/or other highly viscous components) into small droplets, thereby enhancing the reactivity of the liquid fuel feed 304 (by, e.g., increasing the surface area to mass ratio). In the alternative, the liquid fuel feed 304 may be treated in a pre-processing (not shown) that breaks-up the liquid fuel feed as immediately described. Suitable techniques for breaking-up the droplets of highly viscous feedstock include those disclosed in U.S. Pat. Pub. No. 2010/0101978, entitled Flow-Through Cavitation-Assisted Rapid Modification of Crude Oil, filed Oct. 26, 2009, Canadian Pat. Pub. No. 2400188, entitled Method And Device For Resonance Excitation Of Fluids And Method And Device For Fractionating Hydrocarbon Liquids, filed Mar. 22, 2000, and U.S. Pat. Pub. No. 2010/0260649, entitled Deep Conversion Combining The Demetallization And The Conversion Of Crudes, Residues Or Heavy Oils Into Light Liquids With Pure Or Impure Oxygenated Compounds, filed Jun. 28, 2010 (all of which are incorporated in their entireties by reference herein). For relatively lower viscosity liquid fuel feed 304 materials, an industrial homogenizer can be used to break-up the droplets in the liquid fuel feed 304.

The reactor vessel 310 can be a fixed-bed, fluidized-bed, moving-bed, bubble, or slurry catalytic reactor. The catalyst can be supported on a zeolite and include a single transition metal or a combination of transition metals in the form of metal salts, pure metals, and/or metal alloys. Transition metals having atomic numbers ranging from 23 to 79 are preferred, and those with atomic numbers ranging from 24 to 74 are more preferred. In addition, other non-transition metals can be used in place of or in combination with the transition metal catalysts (e.g., aluminum). The catalysts can be in the form of pellets, granules, wires, mesh screens, perforated plates, rods, and or strips. In one illustrative implementation, a catalyst mixture includes aluminum wire, cobalt wire (an alloy containing approximately 50% cobalt, 10% nickel, 20% chromium, 15% tungsten, 1.5% manganese, and 2.5% iron), nickel wire, tungsten wire, and cast iron granules. In another embodiment, the catalyst is in the form of a metal alloy wire. Such metal alloy wires include, without limitation, the transition metals described above including without limitation, organomolybdenum catalysts. The catalysts can be arranged in a fixed or fluid-bed arrangement in combination with gas and liquid distribution manifolds inside the vessel 310. Further more, wire mesh screens (constructed of catalyst materials or otherwise) can be employed within the reactor vessel 310 to promote contact between gaseous reactants and the catalysts.

During operation, the reactor vessel 310 and its contents are maintained at a temperature above ambient temperature and typically below the boiling or decomposition temperature of the liquid phase of the reaction mixture. The vessel 310 is heated using any of known methods for heating reaction vessels, e.g., an internal or external inductive heater, a steam jacket, etc. The reaction is typically operated at or within two atmospheres above ambient pressure.

In some implementations, the reactor vessel 310 includes or enables the creation of an activating energy source for the breaking of C—C and/or C—H bonds in the methane and/or other natural gas components. The activating energy source may include radiation from microwave, infrared, or other sources. In one implementation, a non-thermal plasma is the activating energy source according to the techniques set forth in U.S. Pat. No. 7,494,574, entitled Methods For Natural Gas And Heavy Hydrocarbon Co-Conversion, filed Feb. 3, 2005 (incorporated in its entirety by reference herein).

In other implementations, wires or other point source media are disposed inside the reactor vessel 310 (which may include catalyst materials) such that bubbles and/or liquids flows through the media create electric fields and voltage potentials in the liquid and gas phases in the reactor. Thus, the spacing of the wires, particles, and/or plates causes the creation of energy for activating the methane and other reactants in bubbles in the intimate proximity of the catalyst. Utilizing the electrostatic voltage generated by flowing bubbles and/or liquids in multiphase turbulent flow, thus, provides the activating energy useful if driving the reactions. In an embodiment, the techniques disclosed in *Two Phase Streaming Potentials* (S. S. Marsen, Pet. Eng. Dept., Stanford University; M. W. Wheatall, ARCO International) (incorporated in its entirety by reference herein) can be scaled-up and applied to the reactor vessel 310 to achieve the desired electrostatic voltage for reactant activation.

In still other implementations, sonic energy may be used as a source of activating energy. This may include subsonic, ultrasonic, and or sonic energy in the audible region.

In certain embodiments, oxygen and/or air are included in the light gas 302 or is separately fed to the reactor vessel 310 (separate feed not shown). In these embodiments, the reactor vessel 310 is configured and the reaction conditions are controlled to produce organic oxygenates and/or synthesis gas from the oxygen and natural gas components according to the techniques set forth in *Oxygen Pathways and Carbon Dioxide Utilization in Methane Partial Oxidation in Ambient Temperature Electric Discharges* (D. W. Larkin, T. A. Caldwell, L. L. Laban, and R. G. Mallinson; Energy & Fuels 1998, 12, 740-744) and/or *Partial Oxidation of Methane with Air for Synthesis Gas Production in a Multistage Gliding Arc Discharge System* (T. Sreethawong, P. Thakonpatthanakun, S. Chavadej; Chulalongkorn University; Available online 12 Sep. 2006) (incorporated in their entireties by reference herein).

Gaseous product from the reaction is taken from the headspace of the reactor vessel 310 and fed through a gas phase catalytic reactor 314. In some implementations, reactor 314 contains the same type of catalyst used in reactor vessel 310. Reactor 314 aids in the completion of the reaction(s) between any un-reacted components that may have been carried over from the headspace of vessel 314. The output of reactor 314 passes through heat exchanger 316, including coolant loop 318, to condense at least part of the gaseous reaction product. The heat exchanger 316 and coolant loop 318 are sized to condense and cool the vaporous product resulting from the reactions, as certain of the formed compounds can revert and/or decompose rapidly in the gaseous phase and/or at elevated temperatures. Rapid cooling is preferred to quench products.

The condensed product and remaining vapors pass into a collection vessel 320. The vapors in the headspace 322 of the collection vessel 320 are recycled back to the reactor vessel 310 via a pump/compressor 324 and ejector 326, which can be the same or similar as that described above. Meanwhile, the condensate in the collection vessel 320 comprises the liquid fuel product 328. Reaction byproducts 330 can be removed from the system and further separated via a separator 332. These byproducts can include heavy fractions, alkanes and sulfur compounds. The separator 332 can include a filter, membrane, centrifuge, still, column, and/or other known apparatus for separating liquids and solids as well as separating different liquid fractions from one another.

In one implementation, the separator 332 is a centrifuge that separates solid sulfur compounds from the liquid components (which can include alkanes). The solid sulfur compounds are discarded as waste 334, and at least a portion of the liquid components 336 are passed into a mixer 338 along with a portion of the liquid from the collection vessel 320. The mixer 338 can be any mixer known in the art, such as a splash mixer. The blend produced by the mixer 338 can also be used as a liquid fuel 328.

As noted above, the light gas 302 includes, without limitation, methane, ethane, propane, butane, pentane, hydrogen, carbon dioxide, carbon monoxide, ethylene, ethanol, methanol, or combinations thereof. In some embodiments, water is added to the light gas. In some implementations, the light gas 302 is activated by exposing the light gas 302 to a source of infrared radiation. In some implementations, the radiation is long-wavelength infrared (i.e., light in the 3-8 μm range) and/or mid-wavelength infrared (i.e., light in the 8-15 μm range). However, the use of any wavelengths in the infrared range are within the scope of the invention (e.g., 0.75-1,000 μm). Activation of the light gas is believed to increase the energy of the gas, thereby improving the reaction characteristics of the light gas 302. Thus, the light gas 302 is thought to more completely, and/or more rapidly, react with the liquid fuel feed 304 and/or achieve reactions with higher molecular weight and/or aromatic compounds in the liquid fuel feed 304. In some implementation, the processes set forth in U.S. Pat. No. 7,721,719, entitled Fuel Activation Apparatus for Methane Gas, filed Feb. 16, 2006, and/or U.S. Pat. Pub. No. 2009/0120416, entitled Fuel Activator Using Multiple Infrared Wavelengths, filed Nov. 13, 2007, are used to provide an activated light gas 302 (both are incorporated in their entireties by reference herein).

The liquid fuel feed 304 can include fuels derived from fossil fuels or renewable resources. Examples include one or blends of mineral oil, gasoline, diesel fuel, jet fuel, rocket fuel, petroleum residuum-based fuel oils (e.g., bunker fuels and residual fuels), straight-run diesel fuel, feed-rack diesel fuel, light cycle oil. Liquid fuel feed 304 may also include one or blends of crude oil fractions, including products from hydrocracking, catalytic cracking, thermal cracking, coking, and/or desulfurization processes. Liquid fuel feed 304 may also comprise light straight-run naphtha, heavy straight-run naphtha, light steam-cracked naphtha, light thermally cracked naphtha, light catalytically cracked naphtha, heavy thermally cracked naphtha, reformed naphtha, alkylate naphtha, kerosene, hydrotreated kerosene, atmospheric gas oil, light vacuum gas oil, heavy vacuum gas oil, residuum, vacuum residuum, light coker gasoline, coker distillate, FCC (fluid catalytic cracker) cycle oil, and FCC slurry oil. In some implementations, the liquid fuel feed 304 is activated by exposing the liquid fuel feed 304 to a source of infrared radiation, as described above for the light gas 304. The use of infrared radiation for material activation does not preclude the use of shorter wavelengths to achieve activation, e.g., wavelengths in the nanometer range.

In embodiments in which the light gas 302 and/or the liquid fuel feed 304 are activated by a source of infrared radiation, the source of infrared radiation can be included in the reactor vessel 310. In other implementations, the source of infrared radiation is external to the reactor vessel 310, but is upstream of the reactor vessel. For example, the source of radiation can be immediately downstream of the ejector 308 and immediately upstream of the reactor vessel 310. In further implementations, the source of infrared radiation is upstream of the pump 306 and can be in any of the feeds to the pump 306 (e.g., the light gas 302 feed, the liquid fuel 304 feed, and/or the feed from the homogenizer 313), or in any of the feeds to the homogenizer 313.

Figure 3B:
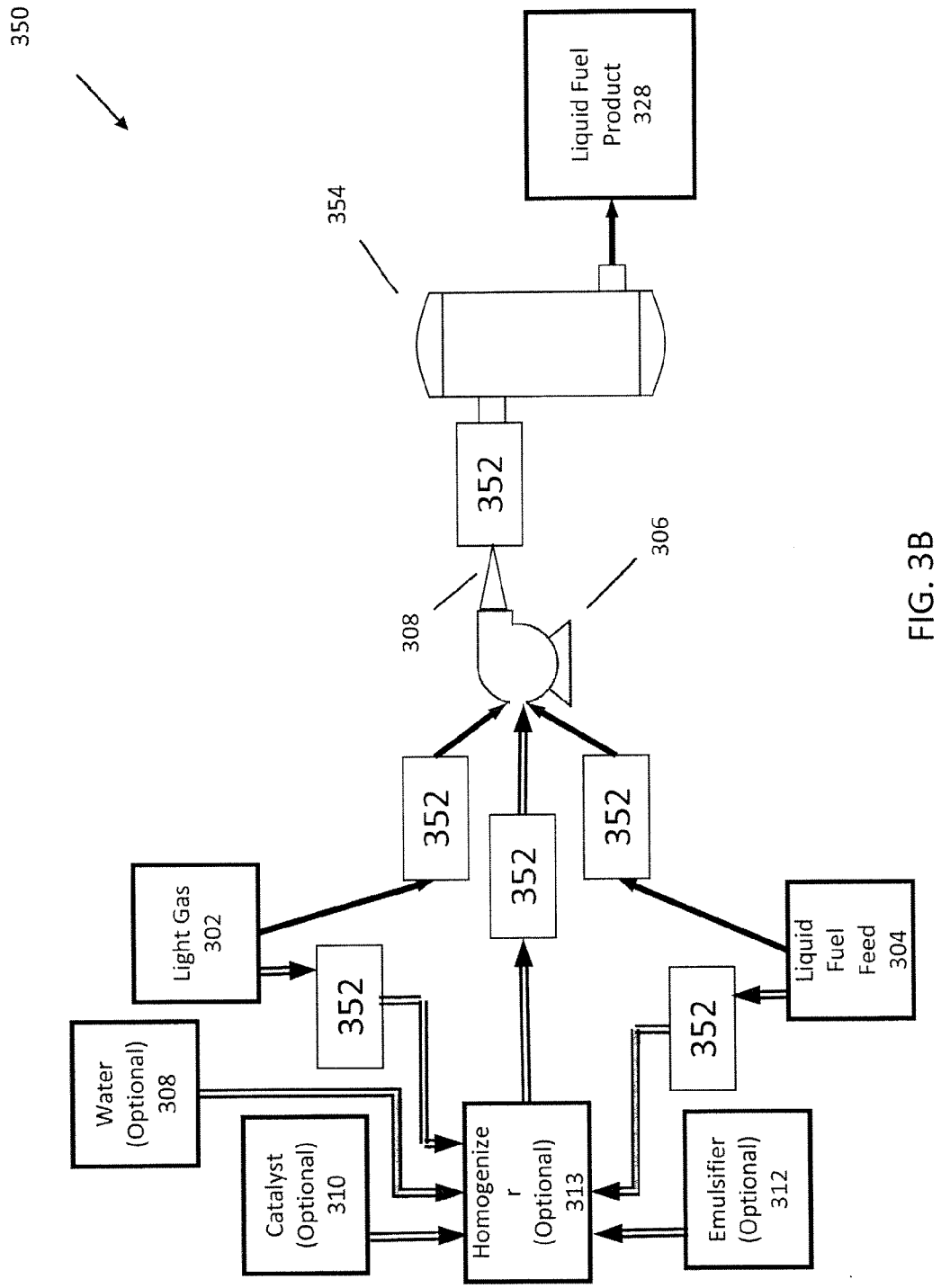
FIG. 3B illustrates a process for producing a liquid fuel product according to one embodiment of the invention.

In another embodiment, the activated light gas 302 and/or liquid fuel feed 304 are not processed in the reactor vessel 310. Rather, they are mixed after or during activation, and the liquid fuel product results therefrom. FIG. 3B shows an overview of an alternate process 350 for making the liquid fuel product 328. The elements of process 350 that share the same reference numerals as the elements of process 300 are the same as those described above. Possible alternative placements of external sources of infrared radiation are shown as radiation source 352 (these correspond to the placements described in connection with FIG. 3A, but are shown on FIG. 3B for ease of illustration). In one implementation, the light gas 302 and/or liquid fuel 304 are activated as set forth above (e.g., upstream of pump 306 or downstream of ejector 308), mixed in pump 306, and ejected into a settling tank 354. The liquid bottoms of settling tank 352 are the alternate liquid fuel product 328. In another implementation, the source of infrared radiation is in settling tank 354. In yet further embodiments, the light gas 302 and liquid fuel 304, either one or both of which can be activated, can simply be mixed and provided as the alternate liquid fuel product.

As mentioned above, it is believed that activating the light gas 302 and/or the liquid fuel feed 304 causes the materials to become more reactive, thereby increasing the speed of reaction of the components. It is hypothesized that activating the materials modifies the stereochemistry of the reactants, which permits reactions that would otherwise not occur to take place. In addition, it is thought that activating the reactants increases the effectiveness of catalysts. Further still, it is postulated that activated reactants can be emulsified without the need for an emulsifier or surfactant. The techniques and apparatus set forth in *Photoassisted Activated of Methane Over Supported Catalysts With a Xenon Excimer Lamp* (Loviat, F., ETH Zürich, 2009), *Bond-and Mode-Specific Reactivity of Methane on Ni*(100) (Maroni, P., École Polytechnique Fédérale De Lausanne, 2005), *Infrared-Excitation for Improved Hydrocarbon Fuel's Combustion Efficiency* (Wey, A., Handy, R. G., Zheng, Y., and Kim, C., SAE International, 2007) (all incorporated in their entireties by reference herein) can be used to achieve the activated reactants.

In some implementations of process 300, the techniques disclosed in U.S. Pat. Pub. No. 2009/0249682, entitled Conversion of Biogas to Liquid Fuels, filed Apr. 7, 2008, U.S. Pat. No. 7,806,947, entitled Liquid Hydrocarbon. Fuel from Methane Assisted by Spontaneously Generated Voltage, issued Oct. 5, 2010, and/or U.S. Pat. No. 7,897,124, entitled Continuous Process and Plant Design for Conversion of Biogas to Liquid Fuel, filed Sep. 18, 2008 (all incorporated in their entireties by reference herein) can be used to provide the liquid fuel product 328.

It is proposed that under certain operating conditions, process 300 enables the direct conversion of the light gas 302 to a liquid fuel in which certain light gases, e.g., methane, behave as a source of hydrogen for the upgrading of various oils and liquid fuel feedstocks. Similarly, some have theorized that a relatively longer chain alkane (A) can be reacted with methane to produce two relatively shorter chain alkanes (B, C) according to Equation 1.

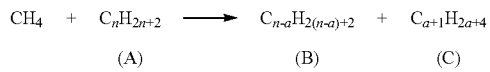

Equation 1

$$CH_4 + C_nH_{2n+2} \longrightarrow C_{n-a}H_{2(n-a)+2} + C_{a+1}H_{2a+4}$$
$$(A) \qquad\qquad (B) \qquad\qquad (C)$$

This "methane-olysis" catalytic reaction (Equation 1), as it is sometimes called, results from bringing methane into contact with at least one other starting alkane (A) having n carbon atoms with n being equal to at least 2, preferably to at least 3, so that the catalytic reaction generally results in the formation of at least one final alkane (B) or of at least two final alkanes (B, C) having a number of carbon atoms ranging from 2 to (n−1) or even to a value greater than (n−1). This is because the alkane or alkanes resulting directly from the methane-olysis reaction can themselves participate in at least one reaction for the metathesis of other alkanes. The use of the word alkane does not preclude applicability to other fractions, e.g., aromatics, alkenes, etc.

It is known that methane can be one of the starting feedstocks for synthetic liquid fuel generation. For example, methane and steam can reformed to create hydrogen and carbon monoxide. The hydrogen and carbon monoxide are then reacted in a Fischer-Tropsch process to create liquid fuels. However, the capital expenditure needed for a Fischer-Tropsch plant is at least an order of magnitude higher than that needed for the presently disclosed process. Moreover, the present process is up to 30% more efficient than a Fischer-Tropsch process.

Moreover, by directly coupling methane (and/or other natural gas components) to hydrocarbon and/or bio-derived fractions and/or consuming the methane in an alkane-alkane reaction, natural gas that is available for use (and which might otherwise be flared) is converted to a liquid fuel. In addition, process 300 reduces the aromatic hydrocarbon and, particularly, polycyclic aromatic hydrocarbon (PAH) content of the final fuel product. PAHs in diesel and jet fuels possess a number of undesirable properties, such as very poor ignition characteristics and cetane numbers, unfavorable cold-flow properties, a propensity for soot formation and a very low hydrogen content. This results in high specific carbon dioxide emissions from the engine.

The maximum level of PAHs permitted in diesel fuels is regulated in many countries, and some countries are proposing to lower those limits. Thus, certain refinery streams which contain relatively high levels of PAHs, such as light cycle oils from fluid catalytic cracking or middle distillate fractions from delayed or fluid cokers, can only be blended into diesel fuel in a limited amounts. The issue of PAH content in fuels will be aggravated when significantly larger portions of non-conventional, hydrogen poor heavy oils will be processed in the future, such as bitumen from oil sands or ultra-heavy oils of the Orinoco type. Selective hydrode-cyclization of PAHs occurring in middle distillates into hydrogen-rich, high-value fuel components, like one-ring naphthenes or, preferably, alkanes, without degradation of the carbon number continues to be a major challenge of heterogeneous catalysis. Thus, the processes set forth herein provide ways to use otherwise troublesome feedstocks to produce fuels with relative low PAH content.

Further still, embodiments of process 300 provide a fuel product that has an improved viscosity and reduced cloud point relative to the raw liquid fuel feed. Process 300 also removes sulfur from the raw liquid fuel feed.

Figure 4:
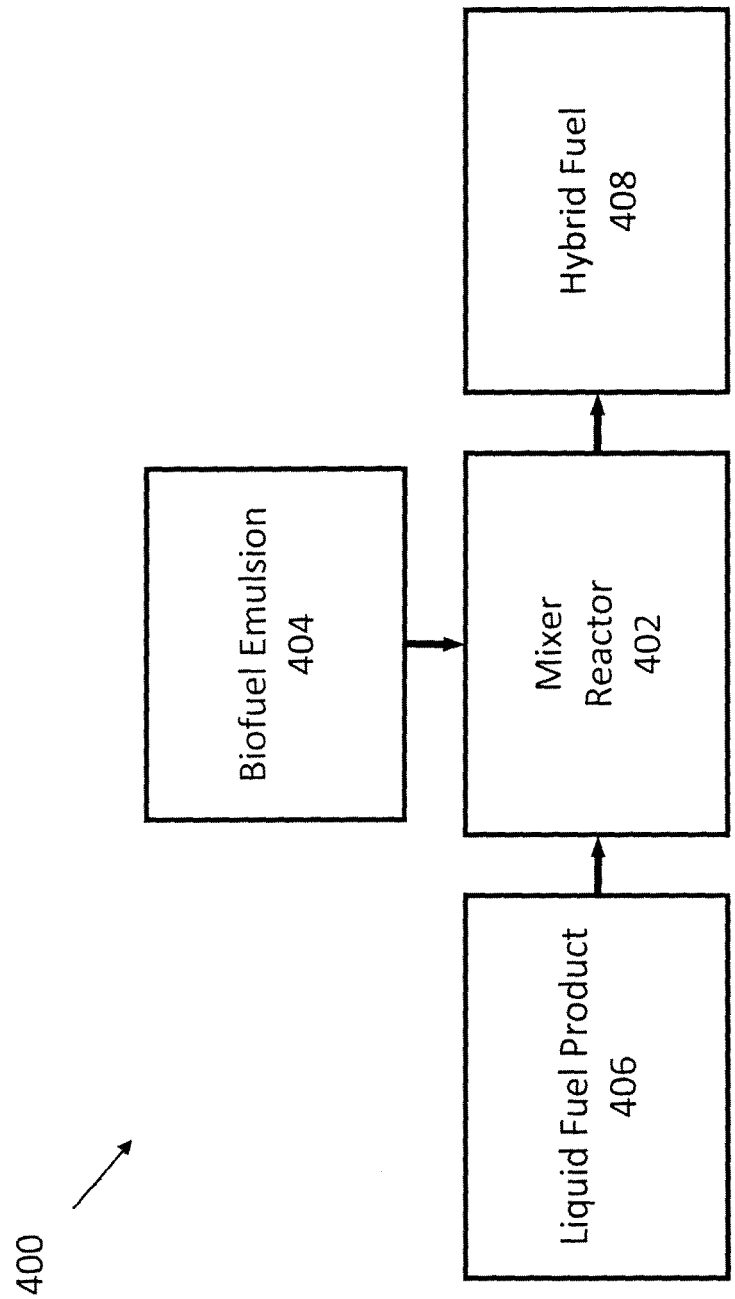
FIG. 4 illustrates a further process for producing a hybrid fuel according to one embodiment of the invention.

FIG. 4 shows a biofuel emulsion and liquid fuel mixing process 400. In embodiments of integrated process 100, process 400 can be used as the biofuel emulsion and liquid fuel mixing process 106. Process 400 includes a mixer reactor 402 to which a biofuel emulsion product 404 and a liquid fuel product 406 are fed to produce a hybrid fuel product 408. The biofuel emulsion product 404 and liquid fuel product 406 can be produced by any of the embodiments described above. Mixer reactor 402 can be any type of mixer (e.g., splash blender) appropriate to the feedstock. In process 400, the biofuel emulsion 404 is blended with the liquid fuel 406 at about 0.5% to about 20% by volume. Blending biofuel with liquid fuel results in several beneficial properties for the hybrid fuel. The addition of biofuel also improves lubricity of the fuel, also reduces the viscosity of the resulting hybrid fuel, and lowers the pour point.

Figure 5:
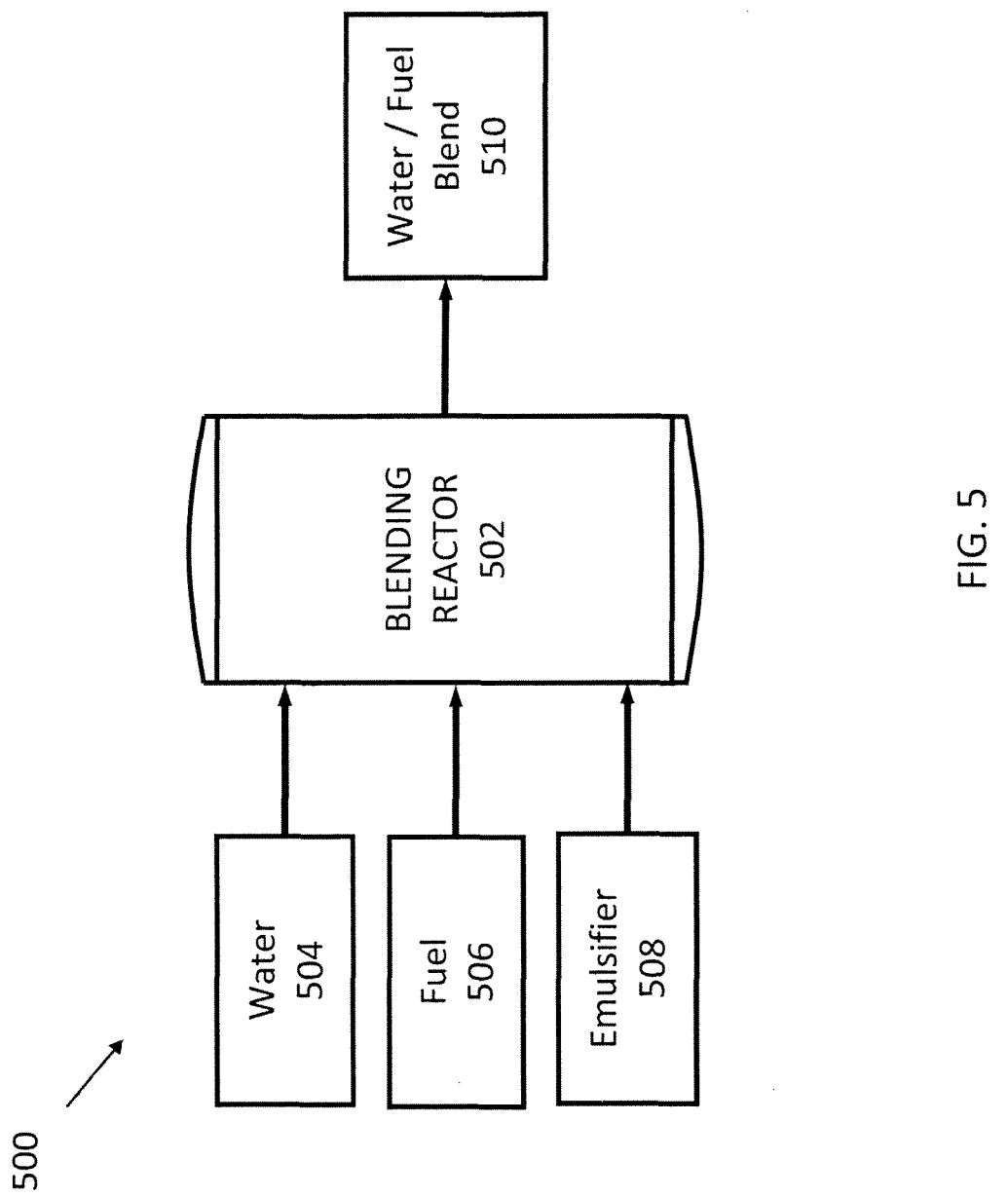
FIG. 5 illustrates a process for producing a water and oil blend product according to one embodiment of the invention.

FIG. 5 shows a process 500 for producing a water/fuel blend product 508 (also called water-in-oil (W/O) product). In embodiments of integrated process 100, process 500 can be used as the water/fuel mixing process 108. Process 500 includes a blending reactor 502 to which water 504, a fuel product 506, and, optionally, an emulsifier 508 are fed to produce a water/fuel blend 510. The fuel product 506 can be a biofuel emulsion 404 and/or a liquid fuel 406, as described above. The blending reactor 502 disperses the water 504 into the continuous phase of fuel 506.

In some implementations, blending reactor 502 includes an electrolytic cell, an ultrasonic wave generator and transducer, and/or a stirring device. In such case, the techniques and apparatus disclosed in U.S. Pat. Pub. No. 2010/0095580, entitled Emulsion Fuel, and Process And Apparatus for Production Thereof filed Jun. 15, 2007, (incorporated in its entirety by reference herein) are used to blend the water 504, the fuel product 506, and the emulsifier 508. Meanwhile, other implementations use the techniques and apparatus set forth in U.S. Pat. Pub. No. 2010/0122488, entitled Oil Emulsion, filed Apr. 4, 2008, (incorporated in its entirety by reference herein) to form the blend 510. As discussed in that application, certain ion exchange resins and mineral substances (e.g., tourmaline and silicon dioxide) are used to pre-treat the water to be used in the process. These materials and techniques are used in embodiments of the present invention also.

In further implementations, blending reactor 502 includes a micronization device, for example, any of the commercial nanomizer products sold by Nanomizer, Inc. of Yokohama, Kanagawa, Japan. The techniques for use and further details of such apparatus are disclosed in U.S. Pat. Pub. No. 2010/0186288, entitled Method for Production of Emulsion Fuel and Apparatus for Production of the Fuel, filed Aug. 31, 2007. In addition, surfactants that are commercially available from Nanomizer, Inc. (e.g., Nanoemer GFA-001) are used in certain implementations of process 500 for the emulsifier 508. The optional emulsifier 508 is selected based on the fuel composition to be emulsified. Even differences of oil origination can affect performance.

In still further embodiments, blending reactor 502 is a high shear reactor configured for combining the water 504, fuel product 506, and emulsifier 508. This can be a single device or a plurality of devices in series or in parallel. In general, a high shear reactor is a mechanical device capable of producing submicron and micron-sized bubbles and/or droplets in a reactant mixture flowing through the high shear reactor. High shear reactors mix the reactant mixture components by disrupting the fluid and/or gas particles of the mixture. High shear reactor can be any one or more of homogenization valve systems, colloid mills, and/or high speed mixers.

In homogenization valve systems, fluid to be processed is pumped under very high pressure through a narrow-gap valve into a lower pressure environment (as described above). The pressure gradients across the valve and the resulting turbulence and cavitation act to break-up any particles in the fluid. High speed mixers usually have paddles, rotors, and/or blades that turn at high speed in a fluid, thereby producing average particle sizes of greater than 20 microns.

Meanwhile, a typical colloid mill configuration includes a conical or disk rotor that is separated from a complementary, liquid-cooled stator by a closely-controlled rotor-stator gap. Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1-25 microns in the processed fluid. These capabilities render colloid mills appropriate for a variety of applications including colloid and oil/water-based emulsion processing.

As stated above, blending reactor 502 disperses the water 504 into the fuel product 506, which is typically the continuous phase. Suitable colloidal mills are manufactured by IKA® Works, Inc. Wilmington, N.C. and APV North America, Inc. Wilmington, Mass., for example. In some implementations, the blending reactor 502 includes the Dispax Reactor® of IKA® Works, Inc. U.S. Pat. Pub. No. 2009/0001316, entitled System and Process for Production of Liquid Product from Light Gas, filed Jun. 17, 2008, (incorporated in its entirety by reference herein) discloses systems and techniques for the use of high shear devices. Any of these techniques and/or systems can be used as a high shear reactor and or any other high shear mixing device disclosed herein.

The stability of the blend 510 depends, at least in part, on the particle size of water 504. The particle size of the water is determined, in part, by the ORP of the water. The goal is to create water droplet size in the blend 508 of 1-5 μm. In some implementations, water 504 is treated to have a negative ORP in the range of about −100 eV to about −500 eV. Water/fuel blends (i.e., emulsions) containing negative ORP water are believed to exhibit excellent efficiency improvements (exceeding 30% increase) over the fuel alone.

Blends of the type described herein have demonstrated significant advantages in engine and heating applications and are believed to result in reduced Greenhouse Gas (GHG), carbon dioxide, hydrocarbon, and $NO_x$ emissions.

Figure 6:
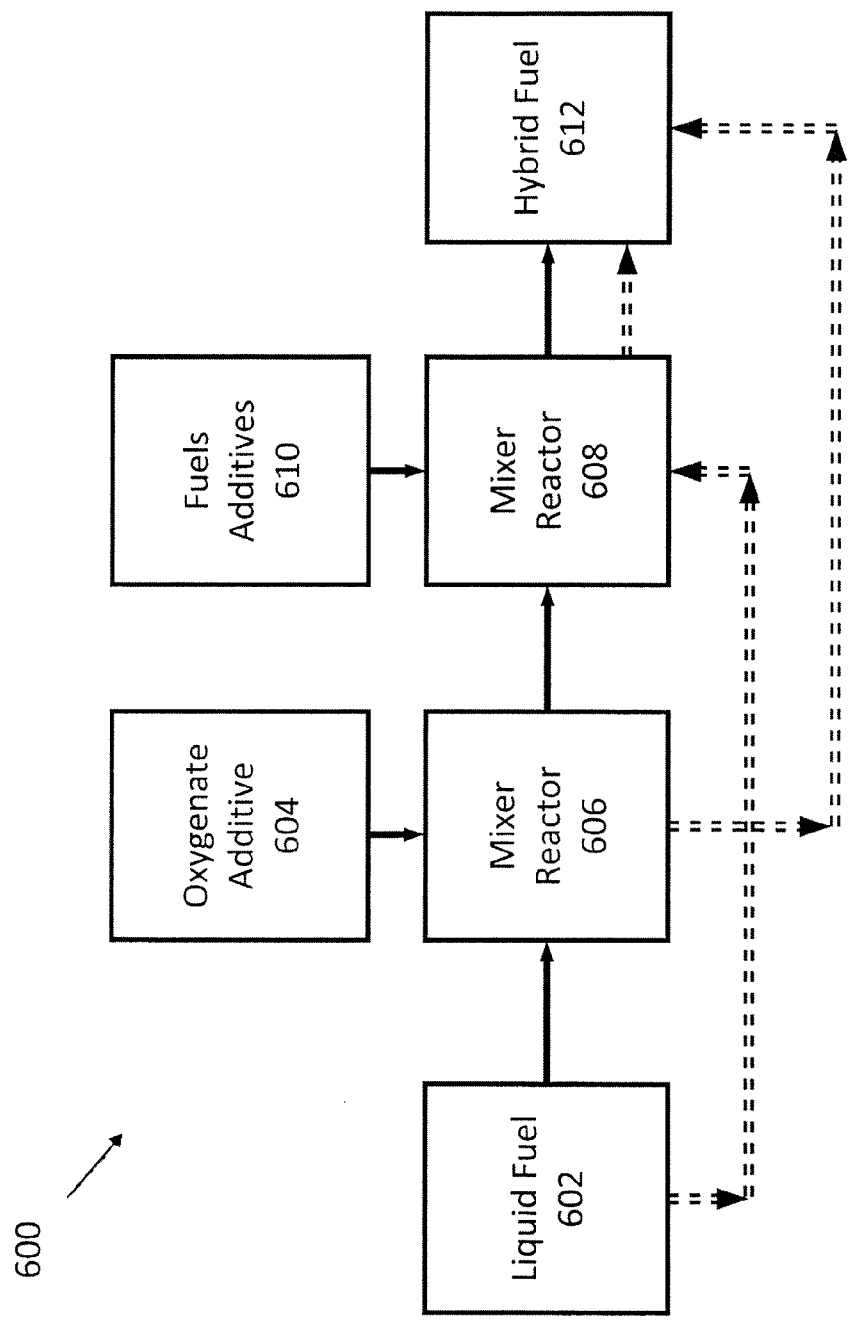
FIG. 6 illustrates an additive package mixing process.

FIG. 6 shows a process 600 for combining a liquid fuel 602 and an oxygenate additive 604 in a mixer reactor 606. The liquid fuel 602 can be any of the liquid fuels described herein, including any implementation of the biofuel emulsions described above. Process 600 also includes a mixer reactor 608 for blending an additive package 610 to produce a hybrid fuel 612. Mixer reactors 606 and 608 can be any mixer known to those skilled in the art, and can include any variety of splash mixer. Mixed reactors 606 and 608 can be a single mixer. As shown in FIG. 6, the process 600 can include the blending of oxygenate additives 604 and other additive packages 610 (as shown in solid lines), or either additive can be omitted (shown in broken double lines).

In some implementations, the oxygenate additive 604 can include commercially available oxygenate additive, such as methyl tert-butyl ether (MBTE), tertiary amyl methyl ether (TAME) ethanol, and others. In other implementations, the biofuel emulsion 222 is used as the liquid fuel 602, in which a blended alcohol serves the purpose of an oxygenate additive, and no further oxygenate is needed. In still further implementations, oxygen and/or carbon dioxide are included in light gas 302 during the manufacture of the liquid fuel product 328, and no further oxygenate is needed. In such an embodiment, the techniques disclosed in U.S. Pat. Pub. No. 2005/0288541, entitled Gas to Liquid Conversion Process, filed Dec. 2, 2004 (incorporated in its entirety by reference herein), can be used to oxygenate the liquid fuel product 328.

In some implementations, the additive package 610 can include any one or more of the following additives: an additive to increase oxidation stability, an additive to adjust viscosity, a rust inhibitor, an additive to adjust lubricity, and/or an additive to enhance a fuel's cetane number. In some embodiments, the additive is a glycol ether. In some embodiments, the additive has the effect of reducing the pour point of the hybrid fuel 612. Specific examples of additives include the following: dimethyl ether (DME), anti-wear additives as disclosed in U.S. Pat. No. 4,185,594, and commercially available cetane boosters.

Referring to FIG. 1, as mentioned above, process 100 is a flexible process, and the above-described sub-processes can be varied or omitted depending on the availability of certain feedstock and/or the desired product. For example, in one embodiment of process 100, a biofuel emulsion from process 102 is reacted with natural gas in process 300. In so doing, it is believed that aromatic hydrocarbons present in the biofuel emulsion are cracked or otherwise transformed into non-aromatic compounds, which enables a more efficient and cleaner-burning fuel relative to the biofuel emulsion alone.

Figure 7:
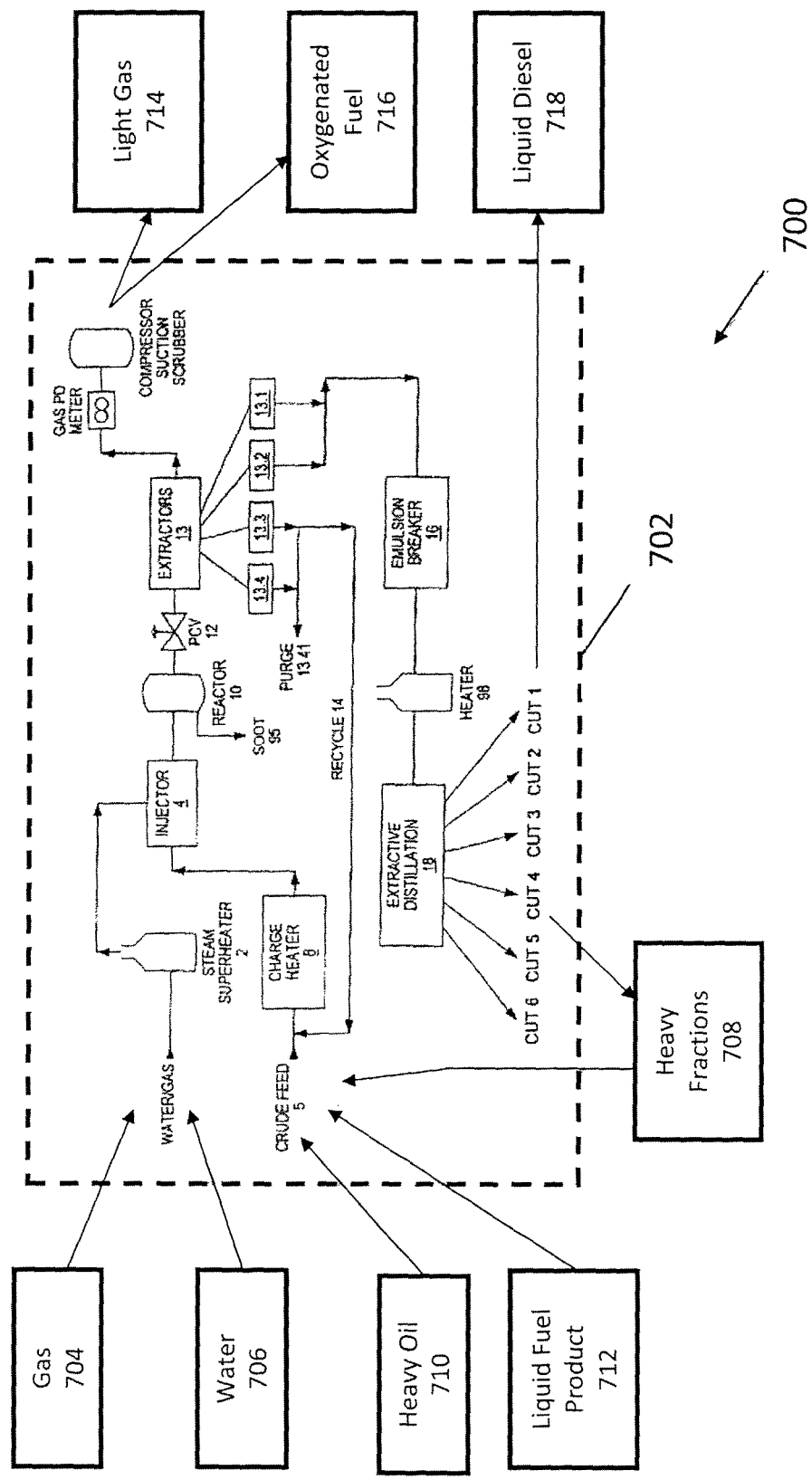
FIG. 7 illustrates a process for producing hybrid fuel feedstocks from heavy oils according to one embodiment of the invention.

FIG. 7 shows a process 700 for producing hybrid fuel feedstocks from heavy oils. As explained above, one aspect of the invention is that the overall process 100 is flexible and can be fully integrated with a variety of processes for oil production, oil refining, fuel production, and/or chemical manufacturing. Process 700 provides an illustrative example of one possible implementation of an integration of process 100 with a process for the conversion into liquids (gasolines, gas oil, fuels) of hydrocarbons that are solid or have a high boiling temperature, laden with metals, sulfur, sediments, with the help of water or oxygenated gas, shown generally as process 702. Process 702 is described in detail in U.S. Pat. Pub. No. 2010/0260649. As explained therein, the process 702 comprises preheating a feed 5 in a heater 8 to a temperature below the selected temperature of a reactor 10. This feed is injected by injectors 4 into the empty reactor 10 (i.e., without catalyst.) The feed is treated with a jet of gas or superheated steam from superheater 2 to activate the feed. The jet of gas may be, for example, from gas 704, which can include carbon dioxide. The activated products in the feed are allowed to stabilize at the selected temperature and at a selected pressure in the reactor and are then run through a series of extractors 13 to separate heavy and light hydrocarbons and to demetallize the feed. Useful products appearing in the form of water/hydrocarbon emulsions are generally demulsified in emulsion breaker 16 to form water laden with different impurities. The light phase containing the final hydrocarbons is heated in heater 98 and is separated into cuts of conventional products, according to the demand for refining by an extractor 18 similar to 13.

Heavy fractions 708 from extractor 18 can be recycled to the process as crude feed 5. In addition, heavy fraction 708 can be used as liquid fuel feed 304 in process 300. Moreover, other heavy oil 710 and/or a liquid fuel product 712, such as any described above, can be supplied as crude feed 5. Thus, in this way, intermediate and/or final products from process 100 can be integrated as feed for process 702.

In addition to integrating materials produced by process 100 into process 702, embodiments of the invention integrate materials produced by process 702 into process 100. For example, a light gas product 714 can be produced as a product from the extractors 13. The light gas product 714 can be used as the light gas feedstock (e.g., light gas 302 of process 300) for any of the liquid fuel processes described herein. Similarly, an oxygenated fuel 716 can be produced as a product from the extractors 13. In some implementations, the oxygenated fuel 716 can be integrated into process 100 in substitution for the biofuel emulsion 102. Similarly, in some implementations, a liquid diesel fuel 718 can be used as a liquid fuel feed 304 in process 300.

Figure 8:
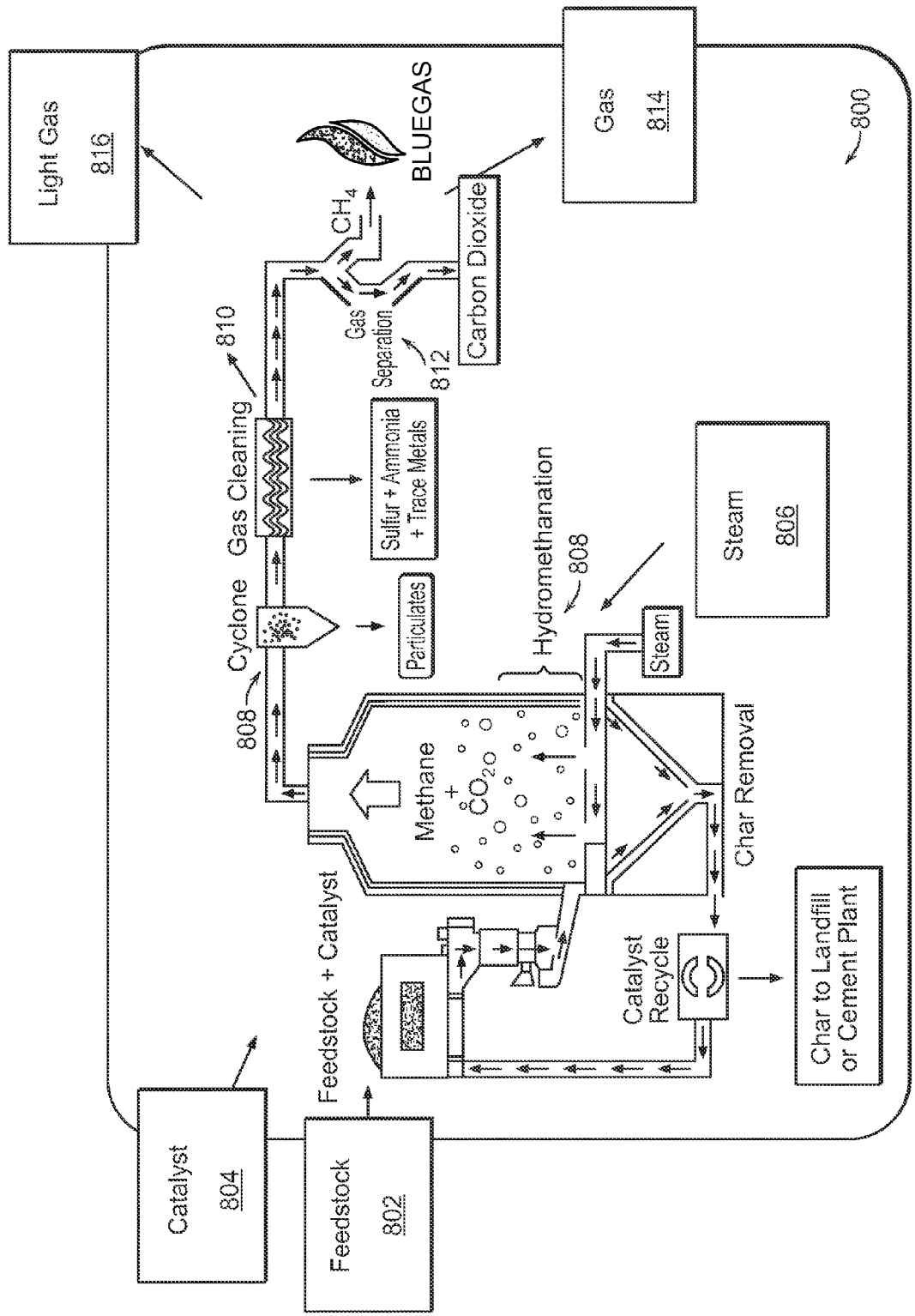
FIG. 8 illustrates a further process for producing hybrid fuel feedstocks from carbonaceous materials according to one embodiment of the invention.

FIG. 8 shows a process 800 for producing feedstocks from carbonaceous materials for use in the hybrid fuel processes disclosed herein. In process 800, a carbonaceous feedstock 802, such as coal, biomass and/or petroleum coke, a catalyst 804, such as an alkali metal, and steam 806, is supplied to a hydromethanation reactor 808. Reactor 808 produces a plurality of gases, including methane, by the reaction of the feedstock in the presence of the catalyst and steam at elevated temperatures and pressures. Fine unreacted carbonaceous materials are removed from the raw gas product by, e.g., a cyclone 810 and the gases are cooled and scrubbed in multiple processes 810, 812 to remove undesirable contaminants and other side-products 814 including carbon monoxide, hydrogen, carbon dioxide and hydrogen sulfide, to produce a light gas stream 816, which includes methane. Exemplary carbonaceous feedstock materials, include without limitation cellulosic feedstock (i.e., wood chips).

The hydromethanation of a carbonaceous materials to methane typically involves four separate reactions:
Steam carbon: $C+H_2O \rightarrow CO+H_2$
Water-gas shift: $CO+H_2O \rightarrow H_2+CO_2$
CO Methanation: $CO+3H_2 \rightarrow CH_4+H_2O$
Hydro-gasification: $2H_2+C \rightarrow CH_4$ In the hydromethanation reaction, the result is a "direct" methane-enriched raw product gas stream, which can be subsequently purified and further methane-enriched to provide the final light gas product 816. This is distinct from conventional gasification processes, such as those based on partial combustion/oxidation of a carbon source, where a syngas (carbon monoxide+hydrogen) is the primary product (little or no methane is directly produced), which can then be further processed to produce methane (via catalytic methanation, see reaction) or any number of other higher hydrocarbon products. When methane is the desired end-product, the hydromethanation reaction provides the possibility for increased efficiency and lower methane cost than traditional gasification processes. In some implementations, the techniques disclosed in U.S. Pat. Pub. No. 2010/0292350, entitled Processes for Hydromethanation of a Carbonaceous Feedstock, filed May 12, 2010, (incorporated in its entirety by reference herein) are employed as process 800.

Process 800 can be integrated with processes 300 and 700 such that the light gas 816 produced by process 800 can be the light gas 302. Similarly, the carbon dioxide from side-products 814 can be the gas 704 used by process 700. Likewise, the heavy fractions 708 from process 700 can be the carbonaceous feedstock 802 for process 800.

FIGS. 9A-9D depict different embodiments of the non-thermal plasma reactors described herein. In these embodiments, syngas is generated via non-thermal plasma techniques. Radicals produced from the production of syngas are utilized directly in subsequent reactions with oil. In certain embodiments, the non-thermal plasma is gliding arc plasma. Gliding arc plasma uses dynamic discharge to create the plasma while the corona discharge generates the plasma with a static discharge. In certain embodiments, the gliding arc has two diverging electrodes. An arc is formed where the gas enters by applying a high voltage. The gas pushes the arc down the length of the reactor. As the gas reaches the end of the reactor, the arc is turned off. Another arc is then formed at the gas entrance.

Figure 9A:
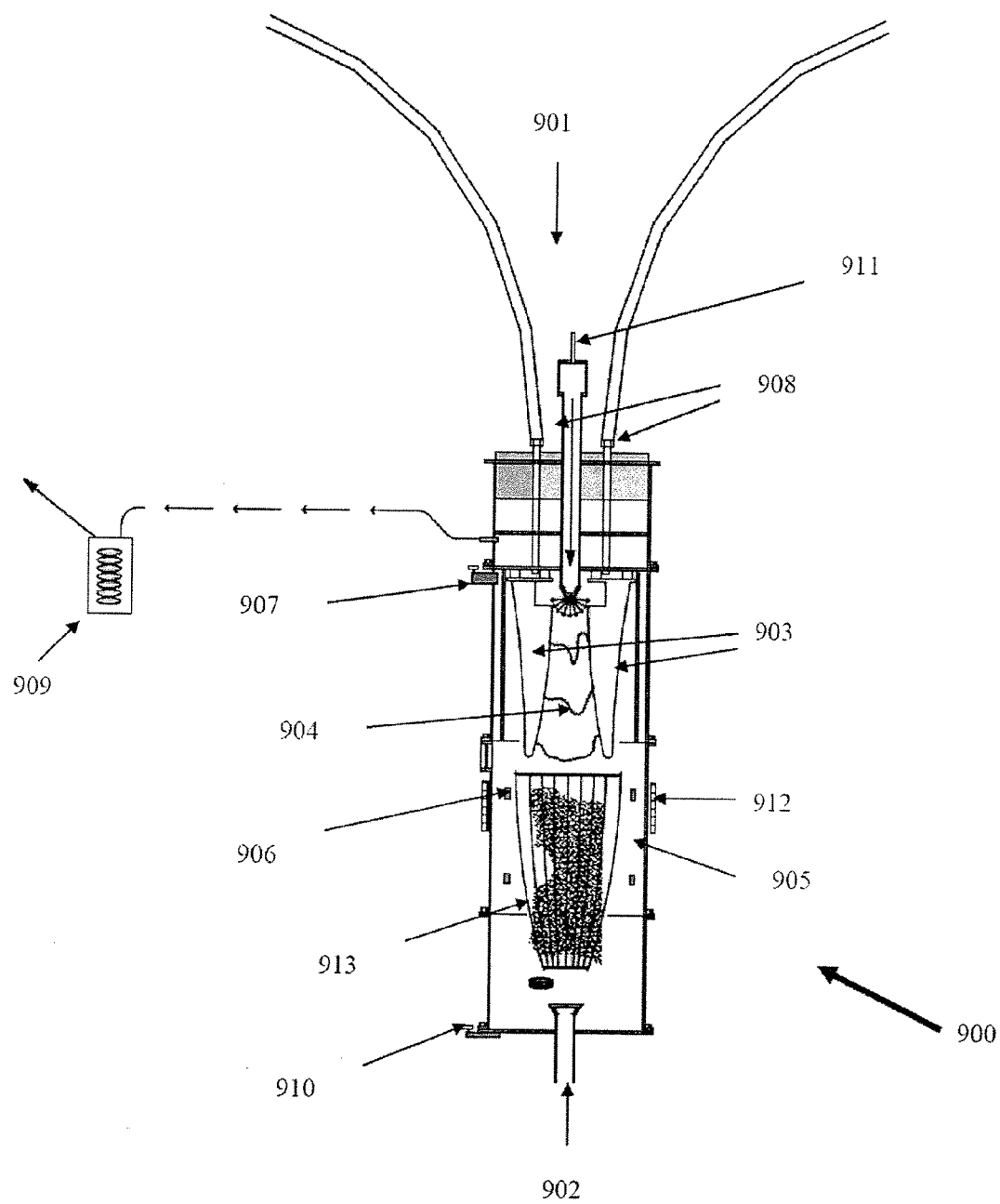
FIG. 9A illustrates a reactor configuration for producing a liquid fuel product according to one embodiment of the invention.

FIG. 9A shows an apparatus 900 for producing a liquid fuel product, in particular for producing a hybrid fuel. In the embodiment depicted, apparatus 900 is a gliding arc reactor, which is a specific embodiment of a non-thermal plasma reactor. In the embodiment depicted in FIG. 9A, liquid and gas are co-processes through the reactor. The plasma is acting simultaneously on the liquid and the gas. In embodiments of integrated process 100, apparatus 900 can be used to produce the light gas/liquid fuel process 104. Similarly, in the embodiments of process 300, apparatus 900 can be used for reactor vessel 310, including, in some embodiments, pump/compressor 306 and ejector 308. Similarly, in process 350, the apparatus 900 can be used for activation source 352.

Apparatus 900 includes an inlet 901 for introduction of a light gas, liquid fuel (e.g., alcohol or oil), or mixture thereof. Apparatus 900 further includes electrodes 903 and high voltage connectors 908. High voltage connectors 908 are connected to an electricity source and supply voltage to electrodes 903. In some embodiments, high voltage connectors supply a pulse up to about 90 kV, corresponding to about 20 KW DC to 30 kHz. Electrodes 903 are in fluid communication with inlet 901 (in some embodiments along the path defined by prechamber 911). In certain embodiments, electrodes 903 are low work force cathodes (i.e., made from low work force metals). Exemplary low work force cathodes include, without limitation, thorium. Upon application of voltage from high voltage connectors 908, an electric discharger, or arc, 904 is formed which travels along the length of the electrodes. Apparatus 900 further includes an exit zone 905, which in fluid communication with the path defined by the electrodes. In some embodiments, exit zone 905 optionally includes and is in fluid communication with Helmholz coils 906, heating coils 912 and a catalyst bracket 913. An outlet 910 for heaving oil is also in fluid communication with exit zone 905. A second inlet 902 is provided and is in fluid communication with exit zone 905, such that exit zone 905 is interposed between electrodes 903 and second inlet 902. Apparatus 900 further includes outlet 907. In some embodiments, condenser 909 is configured to collect outgoing fuel oil from the apparatus.

Upon being introduced to apparatus 900 though first inlet 901, liquid fuel travels along the path defined by electrodes 903 and, optionally, prechamber 903. Upon exposure to electrical arc 904, free radicals are formed. Electrical arc 904 pushes the liquid fuel and free radical reaction products along the path defined by electrodes 903 to exit zone 905. In exit zone 905, the free radicals are in intimate contact with liquid introduced to apparatus 900 through second inlet 902, thereby producing a liquid fuel product. In some embodiments, the liquid introduced through second inlet 902 is a recycled liquid, such as recycled oil. In some embodiments, the mixture of the free radicals and the liquid introduced through second inlet 902 is in further contact with catalyst 913. Catalysts useful to be included in apparatus 900 include those described herein. In some embodiments, heating coils 912 provide for heating of the reaction mixture, while in some embodiments, Helmholtz coils 906 generate a magnetic field conducive to promoting the process of forming liquid fuel. The hybrid fuel formed by apparatus 900 is removed from the apparatus through outlet 907. Upon exiting apparatus 900, the resulting hybrid fuel is capable of further processing as defined in integrated process 100.

The configuration of apparatus 900 allows for a process in which the liquid introduced through second inlet 902 is directly in intimate contact with free radicals generated through the exposure of liquid fuel to the electrodes, as the free radicals are being formed. The intimate contact afforded by the configuration of apparatus 900 provides for the immediate combination of the two reactants, without the need for application of additional energy, as in conventional fuel processes. Moreover, it has been found that the hybrid fuel produced from apparatus 900 demonstrates reduced viscosity and increased volume, as well as a lower fraction of polyaromatic compounds.

Figure 9B:
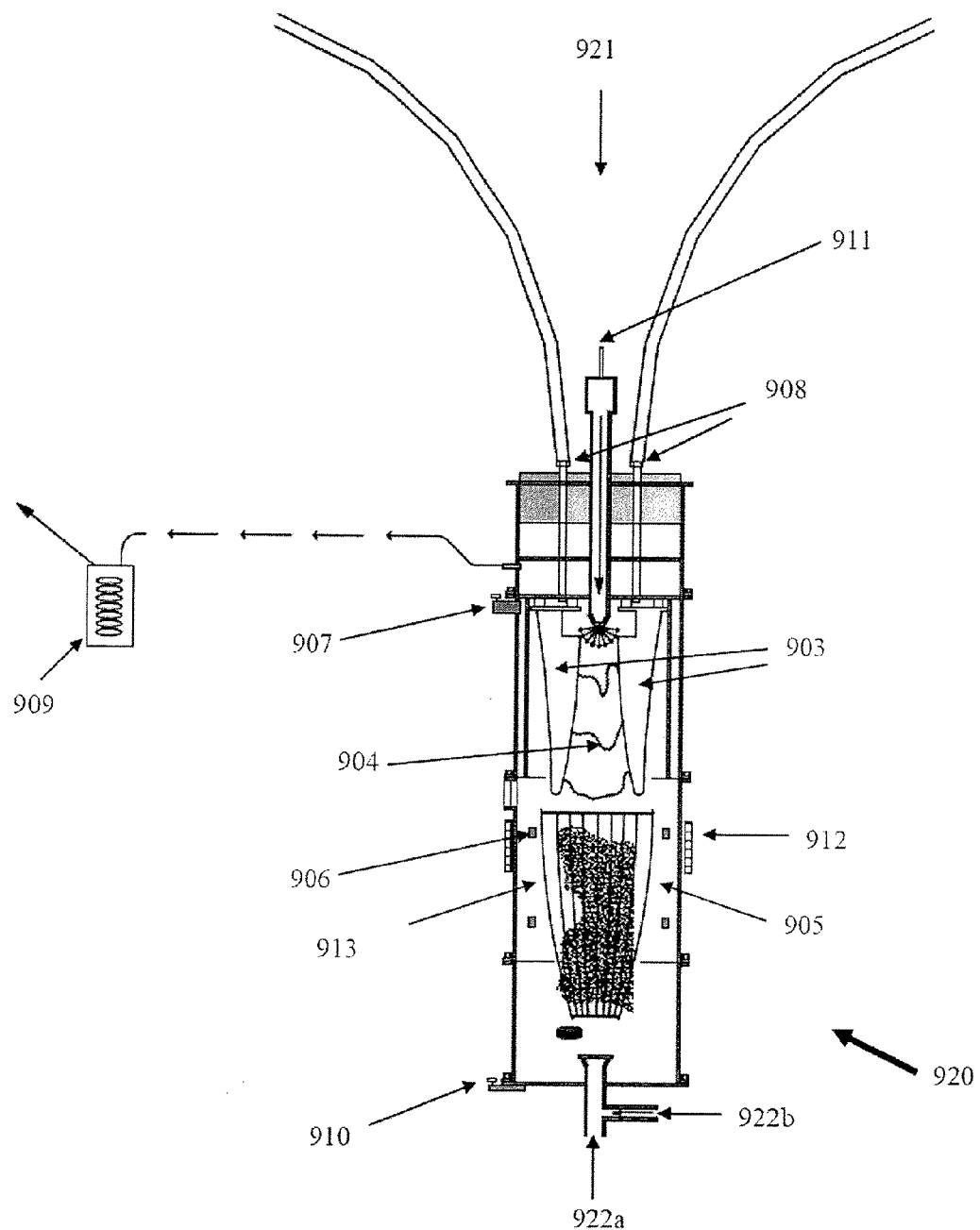
FIG. 9B illustrates a reactor configuration for producing a liquid fuel product according to one embodiment of the invention.

FIG. 9B shows an apparatus 920 for producing a liquid fuel product, in particular for producing a hybrid fuel. In the embodiment depicted, apparatus 920 is another embodiment of a gliding arc reactor, which is a specific embodiment of a non-thermal plasma reactor. In the embodiment depicted in FIG. 9B, the liquid reacts with syngas and radicals, while electron react with liquids in a catalytic contained chamber. As with apparatus 900, in embodiments of integrated process 100, apparatus 920 can be used to produce the light gas/liquid fuel process 104. Similarly, in the embodiments of process 300, apparatus 920 can be used for reactor vessel 310, including, in some embodiments, pump/compressor 306 and ejector 308. Similarly, in process 350, the apparatus 920 can be used for activation source 352.

Apparatus 920 includes many of the same features of apparatus 900, including electrodes 903, which upon application of voltage through high voltage connectors 908, creates arc 904. Similarly, apparatus 920 includes exit zone 905 which is optionally in fluid communication with catalyst 913, Helmholtz coils 906, and heating coils 912. Apparatus 920 also includes outlet 907 and condenser 909.

Apparatus 920 includes inlet 921. Inlet 921 of apparatus 920 provides for input of light gas. In contrast, inlet 901 of apparatus 900 (see FIG. 9A) provided for input of a mixture of gas and liquid, allowing for coprocessing of liquid and gas through the electrodes of the gliding arc reactor. In apparatus 920, liquid in the form of oil or recycle oil is introduced through second inlets 922a and 922b. In certain embodiments, recycled oil is introduced through input 922a, while input oil is introduced through input 922b. In some embodiments, a soluble catalyst is also introduced through input 922b. Inlets 922a and 922b are in fluid communication with exit zone 905 such that they are available for intimate contact with the products of the gliding arc reactor. For example, in certain embodiments, the liquid reacts with syngas and radicals formed by the non-thermal plasma reactor, while electrons react with liquids in exit zone 905. In certain embodiments, exit zone 905 is a catalytic contained chamber. As with apparatus 920, after the reaction products are mixed to form a liquid fuel product, the hybrid fuel is removed through outlet 907.

Figure 9C:
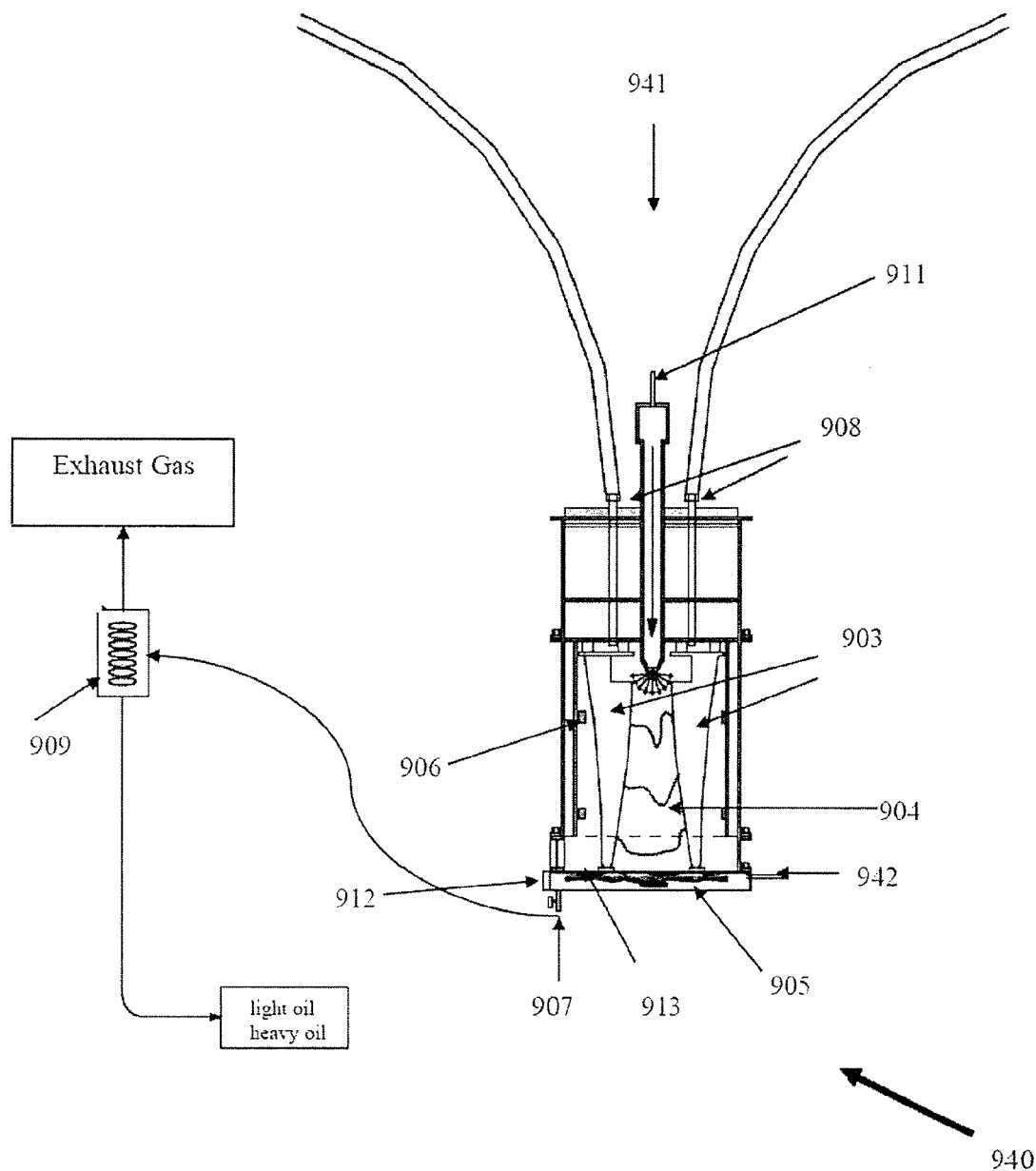
FIG. 9C illustrates a reactor configuration for producing a liquid fuel product according to one embodiment of the invention.

FIG. 9C shows apparatus 940 for producing a liquid fuel product, in particular for producing a hybrid fuel. In the embodiment depicted, apparatus 940 is another embodiment of a gliding arc reactor, which is a specific embodiment of a non-thermal plasma reactor. In the embodiment depicted in FIG. 9C, the syngas and radicals and electrons produced by the gliding arc impinge into a flowing stream of liquid optionally containing a catalyst bed. As with apparatus 900 and 920, in embodiments of integrated process 100, apparatus 940 can be used to produce the light gas/liquid fuel process 104. Similarly, in the embodiments of process 300, apparatus 940 can be used for reactor vessel 310, including, in some embodiments, pump/compressor 306 and ejector 308. Similarly, in process 350, the apparatus 940 can be used for activation source 352.

Apparatus 940 includes many of the same features of apparatus 900 and 920, including electrodes 903, which upon application of voltage through high voltage connectors 908, creates arc 904. In the embodiment of apparatus 940, exit zone 905 is optionally in fluid communication with catalyst bed 913, Helmholtz coils 906, and heating coils 912.

Apparatus 940 includes inlet 941. Inlet 941 of apparatus 940 provides for input of light gas. In apparatus 940, liquid in the form of oil or recycle oil is introduced through second inlet 942. Inlet 942 is in fluid communication with exit zone 905 such that the reaction products from the gliding arc reactor directly impinge the flowing stream of liquid introduced through inlet 942, thereby being in intimate contact with the products of the gliding arc reactor. After the reaction products are mixed to form a liquid fuel product, the hybrid fuel is removed via outlet 907 through separator 909. In some embodiments, separator 909 is also a condenser. In apparatus 940, heavy and light oil exit the system as provided through separator 909.

Figure 9D:
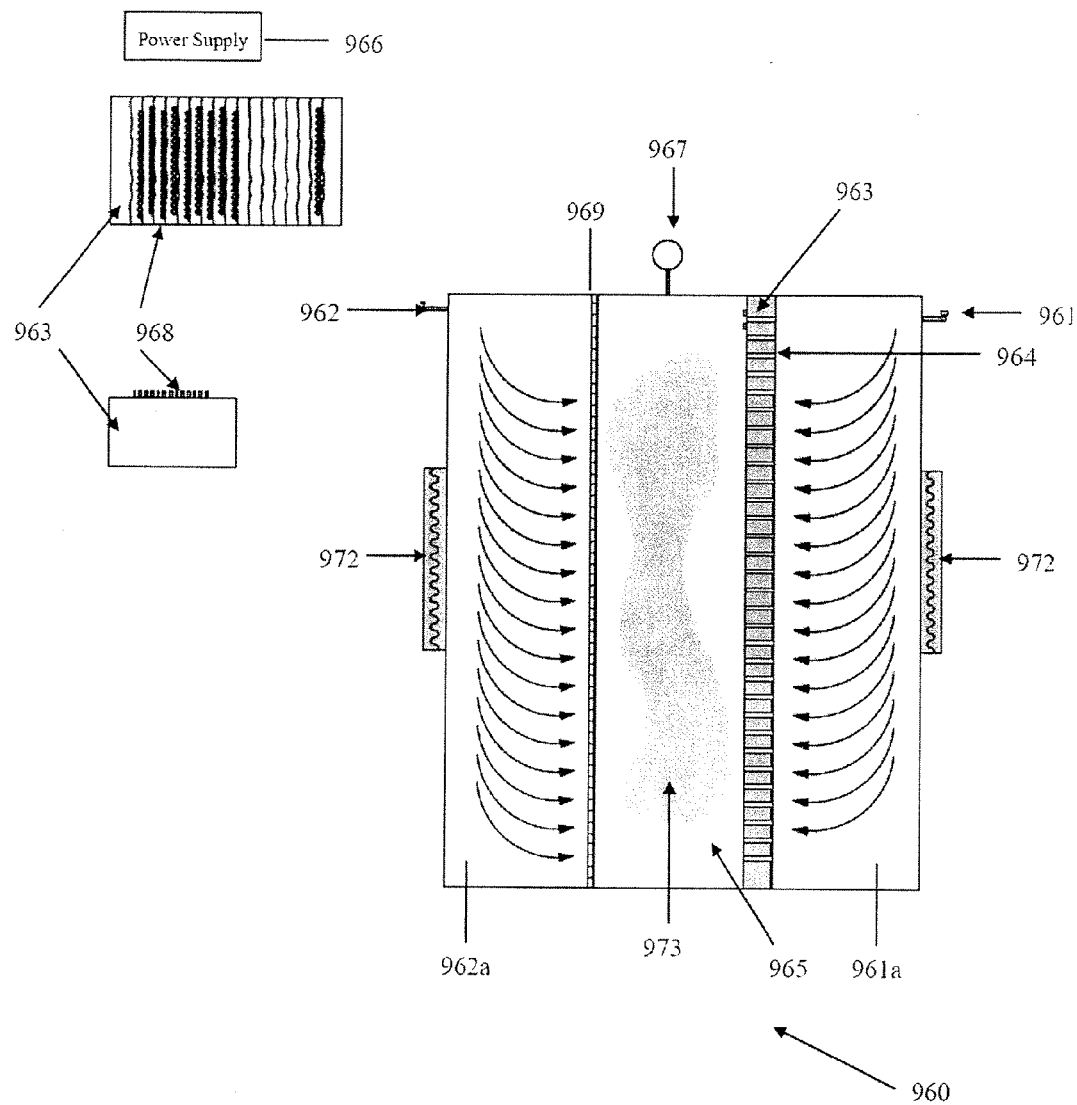
FIG. 9D illustrates a reactor configuration for producing a liquid fuel product according to one embodiment of the invention.

FIG. 9D shows an apparatus 960 for producing a liquid fuel product, in particular for producing a hybrid fuel. In the embodiment depicted, apparatus 960 is a gliding arc reactor, which is a specific embodiment of a non-thermal plasma reactor. In the embodiment depicted in FIG. 9D, the non-thermal plasma reactor is configured as a 'plate' of multiple microplasma reactors. The output of the plate reactors of apparatus 960 impinge on liquid droplets or thin films. In embodiments of integrated process 100, apparatus 960 can be used to produce the light gas/liquid fuel process 104. Similarly, in the embodiments of process 300, apparatus 960 can be used for reactor vessel 310, including, in some embodiments, pump/compressor 306 and ejector 308. Similarly, in process 350, the apparatus 960 can be used for activation source 352.

Apparatus 960 includes an inlet 961 for introduction of light gas into light gas chamber 961a. Apparatus 960 further includes ceramic plate 963, which contains holes 964 through which the gas is dispersed to exit zone 965. Wires 968 are deposited on ceramic plate 963 and are in electrical connection with a power supply 966 for application of voltage (e.g., a 6-1000V pulse). As the gas crosses ceramic plate 963, the applied voltage creates a plurality of arcs in each of holes 964, thereby providing for a reaction with the light gas and causing the formation of free radicals, which are transported into exit zone 965.

Apparatus 960 further includes a second inlet 962 for input of liquid into liquid chamber 962a. In some embodiments; the liquid that is introduced through second inlet 962 is an oil or mixtures of oil. In some embodiments, the liquid introduced through second inlet 962 is a recycled liquid, such as recycled oil. The liquid is transported across diffuser plate 969 to exit zone 965. Upon introduction to exit zone 965, the diffused liquid comes into intimate contact with the reaction products of the light gas that has been transported through ceramic plate 963, thereby producing a hybrid electric fuel product. Optionally, catalyst bed 973 is present in exit zone 965. Also, optional heaters 972 heat apparatus 960. After the reaction products are mixed, they exit the apparatus through outlet 967. In some embodiments, an optional vacuum pump is located between exit zone 965 and outlet 967. Upon exiting apparatus 960, the resulting hybrid fuel is capable of further processing as defined in integrated process 100.

In FIGS. 9A-9D, the configuration of each apparatus 900, 920, 940, and 960 provides for a process in which the liquid is directly in intimate contact with free radicals generated through the exposure of liquid fuel to the electrodes, as the free radicals are being formed. The intimate contact afforded by the configuration of each apparatus provides for the immediate combination of the reactants, without the need for application of additional energy, as in conventional fuel processes. Moreover, it has been found that the hybrid fuel produced from apparatus 900, 920, 940 and 960 demonstrates reduced viscosity and increased volume, as well as a lower fraction of polyaromatic and aromatic compounds.

The hybrid fuels 120 produced by embodiments of process 100 possess superior performance characteristics relative to competing fuels (e.g., biodiesel fuels, "green diesel" fuels, straight vegetable oil fuels, oil/water emulsion fuels, and conventional petroleum fuels). For example, some embodiments of the hybrid fuels can be a drop-in fuel rather than having to be blended with conventional fuels. Certain hybrid fuels have relatively low pour and cloud points, can withstand multiple freeze/thaw cycles, and have relatively long term stability (e.g., greater than 1 year). Thus, certain hybrid fuels disclosed herein are suitable for use in cold weather. In one illustrative example, a hybrid fuel comprising about 20% by volume Next Generation Diesel (commercially available from Global Energy Resources, LLC of Fort Wayne, Ind.) and about 80% by volume GDIESEL™ (commercially available from Advanced Refining Concepts of Reno, Nev.) surprisingly exhibits about a 25° F. (14° C.) reduction in pour point relative to the individual fuel components. This same hybrid fuel also surprisingly exhibits about a 5° F. (3° C.) reduction in cloud point. Accordingly, according to certain embodiments, the hybrid fuel blends disclosed herein include up to about 20% of a biofuel emulsion (e.g., the result of process 102 of FIG. 1 or 222 of FIG. 2). In some embodiments, the hybrid fuel blends disclosed herein include from about 5% to about 10% of a biofuel emulsion. Moreover, in some embodiments, up to about 20% water is present in the hybrid fuel.

A further proposed embodiment of a hybrid fuel includes combining activated natural gas and/or hydrogen with the Next Generation Diesel using process 350 described above. It is thought that such a hybrid fuel would exhibit lower $CO_2$ emissions than the Next Generation Diesel alone due to an increase in the hydrogen to carbon ratio of the fuel.

In certain embodiments of the hybrid fuels disclosed herein, the lubricity and/or viscosity of the liquid fuel is increased by the addition of the biofuel emulsion. Thus, ultra-low-sulfur diesel (ULSD) can be used as the liquid fuel in certain formulations without suffering the disadvantage of the low lubricity and/or low viscosity of the ULSD. Also, the need for an additive to increase lubricity is lessened or avoided along with the increased cost and process complexity of doing so. In some embodiments, the formulations containing ULSD have lower viscosity and pour point than either conventionally hydrotreated ULSD or biofuel emulsion.

Further advantages include that certain hybrid fuels disclosed herein have reduced greenhouse gas emissions, reduced particulate emissions, and have feedstocks comprising materials produced by the consumption of carbon dioxide (e.g., plant oils). Total reduction in emission is expected to be about 50% for certain processes to produce the hybrid fuels. Meanwhile, a reduction of 30% in carbon dioxide and particulate emissions from end use are expected. Thus, the use of such hybrid fuels has a reduced environmental impact. Further still, certain embodiments of the hybrid fuels avoid the transesterification step found in many biodiesel products. Thus, these hybrid fuels will not contain glycerin, fatty acid methyl esters (FAMEs) or fatty acid ethyl esters (FAEEs), which are usually found in at least small amounts in typical biodiesel products. Because regulatory guidelines prohibit the presence of these byproducts in certain fuels (such as jet fuels), these hybrid fuels are suitable for transportation via existing pipeline infrastructure, unlike most common biodiesel products. Moreover, by avoiding the transesterification process, the capital cost, operating cost, complexity, and time involved in that process are avoided. This reduces the cost of producing such hybrid fuels.

The above-described advantages show that embodiments of the invention provide for drop-in fuels that meet ASTM and EU-wide targets on biofuels and greenhouse gas emissions based on Well-to-Wheel considerations and Life Cycle Analysis. Embodiments of the hybrid fuels are considered drop-in in that they can be used as an entire fuel rather than merely as a fuel additive. Because certain liquid hybrid fuels are formed through the use of natural gas, the need for liquid petroleum is reduced. In addition, the processes for the formation of liquid fuels can be adapted to remote locations that presently have natural gas supply that is not being used.

Embodiments of the hybrid fuels formed by implementations of the processes described herein exhibit the desirable characteristics described above while retaining characteristics found in conventional fuels. For example, the hybrid fuels described herein have high energy content per pound/gallon, are able to withstand multiple freeze cycles, are stable, have favorable viscosity and cetane values (for diesel-type fuel replacements), equivalent phosphorous content, compatible distillation curves, favorable corrosion characteristics, and compatibility with existing seal materials.

It will be appreciated that the scope of the present invention is not limited to the above-described embodiments, but rather will encompass modifications of and improvements to what has been described. All references described above are incorporated in their entireties by reference herein.

I claim:

1. A process for the preparation of a modified liquid fuel, the process comprising:
   introducing a first reactant to a reactor, wherein the first reactant comprises one or more light gases;
   exposing the first reactant to non-thermal plasma in the reactor under conditions sufficient to generate at least one activated light gas species;
   introducing a first liquid feed fuel comprising hydrocarbons to the reactor; and
   coupling the activated light gas species to the hydrocarbons by contacting the activated light gas species generated from the first reactant with the first liquid feed fuel in the reactor to produce a modified liquid fuel, wherein the modified liquid fuel has a higher molecular weight than the first liquid feed fuel.

2. The process of claim 1, wherein the modified liquid fuel is a biofuel.

3. The process of claim 1, further comprising steps for refining oil.

4. The process of claim 1, wherein the generating at least one activated light gas species is not preceded by a process for disassociating the one or more light gases.

5. The process of claim 1, wherein the reactor is a non-thermal plasma reactor.

6. The process of claim 5, wherein the non-thermal plasma reactor is a gliding arc reactor, a micro-plasma generator, or a homogenizer.

7. The process of claim 1, further comprising adding a catalyst in the reactor.

8. The process of claim 7, wherein the catalyst is a metal catalyst, an organometallic catalyst, a nanosphere catalyst, a supported catalyst, or a soluble catalyst.

9. The process of claim 8, wherein the catalyst is an organomolybdenum compound.

10. The process of claim 1, wherein the process forms fatty acid ethyl esters (FAEE) and glycerol as byproducts.

* * * * *